United States Patent
Kolber et al.

(10) Patent No.: US 8,156,968 B2
(45) Date of Patent: Apr. 17, 2012

(54) CHASSIS ASSEMBLY

(75) Inventors: John J. Kolber, Erie, CO (US); Donald P. Difka, Erie, CO (US); Gerald Davis, Erie, CO (US)

(73) Assignee: Watermill Express, LLC, Brighton, CO (US)

( * ) Notice: Subject to any disclaimer, the term of this patent is extended or adjusted under 35 U.S.C. 154(b) by 1237 days.

(21) Appl. No.: 11/863,119

(22) Filed: Sep. 27, 2007

(65) Prior Publication Data
US 2008/0073287 A1 Mar. 27, 2008

Related U.S. Application Data

(60) Provisional application No. 60/847,451, filed on Sep. 27, 2006.

(51) Int. Cl.
*B65B 1/04* (2006.01)
(52) U.S. Cl. ............. 141/1; 141/21; 141/192; 141/302; 141/392; 222/748.1; 222/748.11
(58) Field of Classification Search .............. 141/21, 141/192, 301, 302, 392; 222/113, 148; 251/300, 251/301, 205, 208; 210/748.1, 748.11
See application file for complete search history.

(56) References Cited

U.S. PATENT DOCUMENTS

| | | | |
|---|---|---|---|
| 4,501,381 A | 2/1985 | Hart | |
| 4,780,200 A | 10/1988 | Bond | |
| D323,355 S | 1/1992 | Dolifka | |
| D341,627 S | 11/1993 | Dolifka | |
| 5,316,673 A | 5/1994 | Kohlmann et al. | |
| 5,417,083 A * | 5/1995 | Eber | 62/528 |
| 5,582,717 A | 12/1996 | Di Santo | |
| 5,587,089 A | 12/1996 | Vogel et al. | |
| 5,881,913 A | 3/1999 | Boulter | |
| 5,911,884 A | 6/1999 | Boulter | |
| 6,077,427 A * | 6/2000 | Burrows | 210/198.1 |
| 6,216,918 B1 * | 4/2001 | Saveliev et al. | 222/148 |
| 6,405,900 B1 | 6/2002 | Kown | |
| 6,561,382 B2 | 5/2003 | Shelton | |

* cited by examiner

*Primary Examiner* — Jason J Boeckmann
*Assistant Examiner* — Joel Zhou
(74) *Attorney, Agent, or Firm* — William W. Cochran; Cochran Freund & Young

(57) ABSTRACT

Disclosed is a rotary valve and rotary disk fluid dispensing system that sanitizes valve ports using UV radiation during non-use. Steam and ozinated water can also be used for stripping and disinfecting portions of the dispenser that can be accessed by the public. The system also uses detectors including hall detectors and a camera to inspect for blockage of valve ports, tampering or improper operation of the rotary valve disc.

12 Claims, 31 Drawing Sheets

CHASSIS ASSEMBLY

CROSS-REFERENCE TO RELATED APPLICATION

This application is based upon and claims priority to U.S. provisional application Ser. No. 60/847,451, filed Sep. 27, 2006, entitled "Chassis Assembly," the entire disclosure of which is herein specifically incorporated by reference for all that its discloses and teaches.

BACKGROUND OF THE INVENTION

Unmanned dispensers that dispense fluids, foods and other materials can be subject to contamination and tampering. For example, but not by way of limitation, unmanned fluid dispensers, such as water dispensing systems, can be contaminated by users that place their own water containers against the dispensing nozzle and transmit the contamination to other users who place containers against the same nozzle. Further, users may tamper with dispensing nozzles by placing objects in the dispensing nozzle to block the flow of the water. These objects may also contaminate the water source. Of course, this can occur in any type of fluid dispensing device, such as soft drink dispensers, milk dispensers, frozen drink dispensers, etc. Further, food dispensers, such as cereal dispensers, trail mix dispensers, bulk food dispensers, etc., where the public has direct access to these dispensers, are subject to the same problems.

SUMMARY OF THE INVENTION

The present invention may therefore comprise a dispenser for dispensing a fluid to a user at a user into a container access point in a fluid dispensing stream comprising: a point of vend port that dispenses the fluid, the point of vend port disposed in a first isolation chamber; a second isolation chamber that provides spatial separation between the point of vend port and the user access point; a shutter that isolates the first isolation chamber from the second isolation chamber during an idle state; a UV lamp mounted on the shutter that irradiates and sanitizes the point of vend port during the idle state; a rotary disk having at least one vend port and at least one idle port, the vend port aligned with the point of vend port when the dispenser is in a vend state and the idle port aligned with the point of vend port when the dispenser is in an idle state, the rotary disk having at least a clear portion so that the idle port is visible to the user during the idle state and the vend port is visible to the user during the vend state so that the user can align the container with the water dispensing stream during the idle state and the vend state, the rotary disk positioned adjacent to the second isolation chamber to provide a physical barrier between the user access point and the second isolation chamber; a driver that rotates the rotary disk between the idle state and the vend state.

The present invention may further comprise a method of dispensing fluid from a dispenser to a user into a container at a user access point in a fluid stream comprising: isolating a point of vend port that dispenses the fluid from the user access point with a rotary disk that forms a physical barrier between the point of vend port and the user access point; isolating a point of vend port from the rotary disk with a shutter that forms a physical barrier between the point of vend port and the user access point during an idle state of the dispenser; irradiating the point of vend port during the idle state with a UV lamp mounted on the shutter; aligning an idle port in the rotary disk with the point of vend port during an idle state so that the container can be aligned by a user with the fluid stream during the dispensing of the fluid; aligning a vend port in the rotary disk with the point of vend port during a vend state so that the fluid stream passes from the point of vend port through the vend port during the vend state; providing a clear portion in the rotary disk adjacent to the vend port and the idle port so that the vend port is visible to the user during the vend state and the idle port is visible to the user so that the user can align the container with the fluid stream during the idle state; rotating the rotary disk so that the vend port is aligned with the point of vend port during the vend state and the idle port is aligned with the point of vend during the idle state.

The present invention may further comprise a fluid dispensing system for dispensing a fluid comprising: a rotary valve disk having at least two valve ports operatively connected to a main port and opaque sections along an outer surface of the rotary valve disk between the valve ports; a stationary port that dispenses the fluid through a dispensing port in the stationary port; a UV light positioned around the rotary valve disk at a location where the UV light can irradiate at least one valve port of the at least two valve ports that is not dispensing the fluid; a camera located in a position around the rotary valve disk to view at least one of the valve ports of the at least two valve ports that is not dispensing the fluid and is not being irradiated by the UV light.

The present invention may further comprise a method of dispensing fluids comprising: providing a rotary valve disk having at least two valve ports that are operatively connected to a main valve port; placing the main valve port of the rotary valve disk in communication with a stationary port having a dispensing port for communicating the fluid from the main port to the valve ports; irradiating at least one of the valve ports that is not in a position to dispense fluid using ultraviolet radiation; generating an image at least one of the valve ports that is not in a position to dispense fluid using a camera; analyzing an image generated by the camera to determine if a blockage exists in the at least one valve port.

DETAILED DESCRIPTION OF THE EMBODIMENTS

Figure 1:
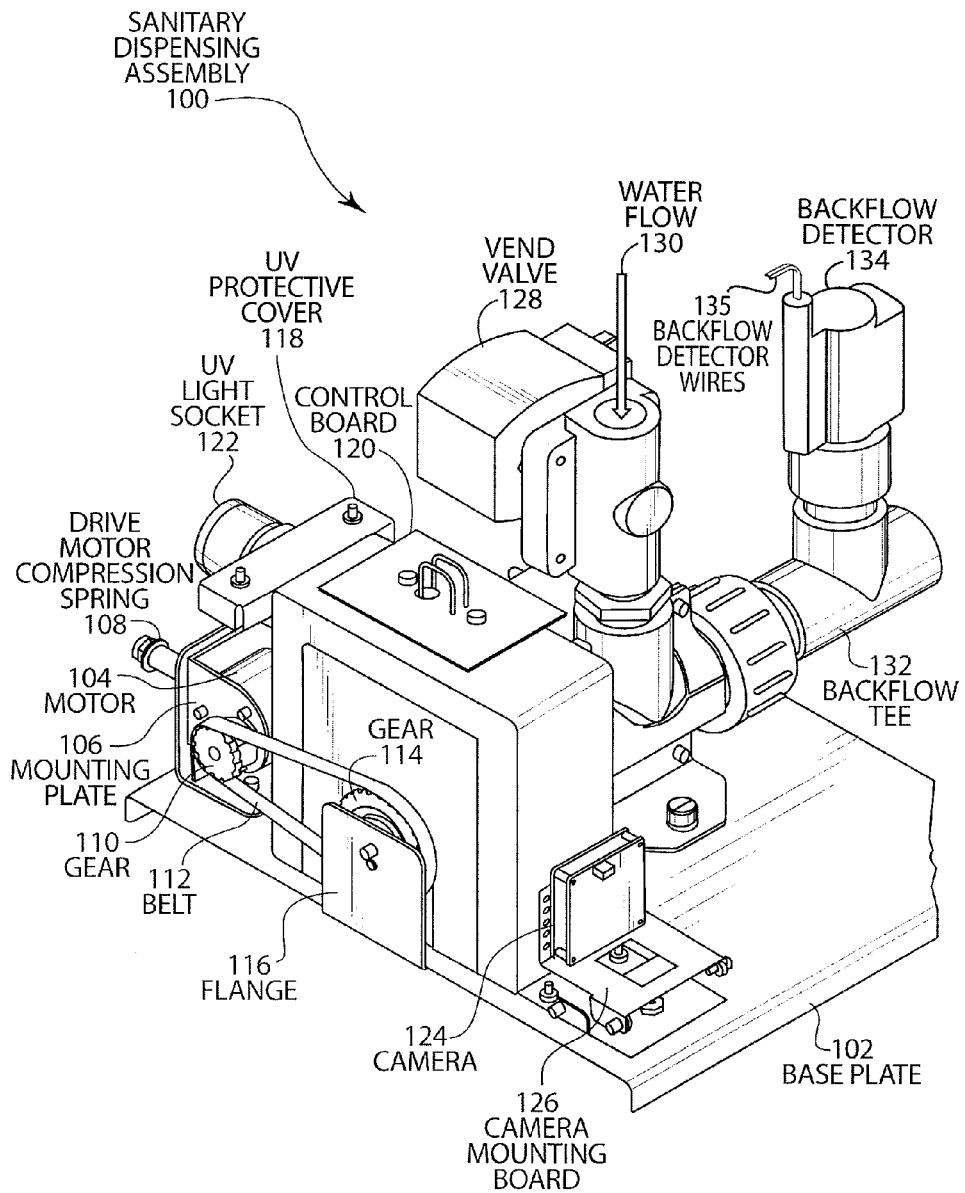
FIG. 1 is a schematic isometric rendering of an embodiment of a sanitary dispensing assembly.

FIG. 1 is a schematic isometric view of one embodiment of a sanitary dispensing assembly 100. The sanitary dispensing assembly 100 is mounted on a base plate 102. The system is driven by an electric motor 104 that is mounted to a mounting plate 106. The mounting plate is attached to a flange, that is in turn attached to the base plate 102. A drive motor compression spring 108 pulls the mounting plate 106 towards the flange to tighten belt 112. The pressure of the drive motor compression spring 108 can be adjusted with the bolt that is attached to the drive motor compression spring 108 and mounting plate 106. The compression created by the drive motor compression spring 108 places tension on the geared belt 112 that is wrapped around the geared drive pulley 110. In this fashion, the tension on the belt 112 is controlled by the pressure created by the drive motor compression spring 108, which is adjustable by rotation of the bolt. As disclosed below, the rotary dispensing valve can potentially be accessed by the general public. If a child inserts a finger in the rotary dispensing valve, it is important that an undue amount of tension is not created on the belt to prevent injury to a user's finger. Hence, the tension on the drive motor compression spring can be adjusted to prevent injuries. FIG. 1 also illustrates the manner in which the belt 112 wraps around the geared pulley 114. The geared pulley 114 is mounted on a flange 116 that is also attached to the base plate 102.

FIG. 1 also illustrates the UV protective cover 118 that houses a rotary valve disk 136 (FIG. 2) and a UV light 184 (FIG. 7) that is used to sanitize the ports of the rotary valve disk 136. The UV light 184 emits high intensity UV-C radiation (approximately 254 nM) that is encapsulated in the UV protective cover 118. UV-C radiation can cause severe skin and eye damage. Hence, the UV-C radiation must be contained within the UV protective cover 118 that encapsulates the UV light 184 and the UV-C radiation from the UV light 184 to prevent damage to users of the sanitary dispensing device. The UV light 184 is mounted in a UV light socket 122 that is attached to the UV protective cover 118. Camera 124 is also aligned with an opening in the UV protective cover on an opposite side from the UV socket 122. Camera 124 has an opening (shown in FIG. 4) in the UV protective cover 118 to view the valve port openings 142, 146 (FIG. 3) when the device is in the rest position, and other positions, as disclosed below. Camera 124 is mounted to a camera mounting board 126 that aligns the camera 124 with the opening in the UV protective cover 118.

FIG. 1 also illustrates the vend valve 128 that opens a port when the user of the dispensing system receives water. Water flows in the direction of arrow 130 into the system through various ports, as disclosed below, for dispensing. Alternatively, if the dispensing system within the UV protective cover 118 is not operational, for any reason, such as the dispensing ports being blocked, water flows through the backflow Tee 132. Water flow through the backflow Tee 132 is detected by the backflow detector 134 which sends a signal to the system via the backflow detector wires 135.

Figure 2:
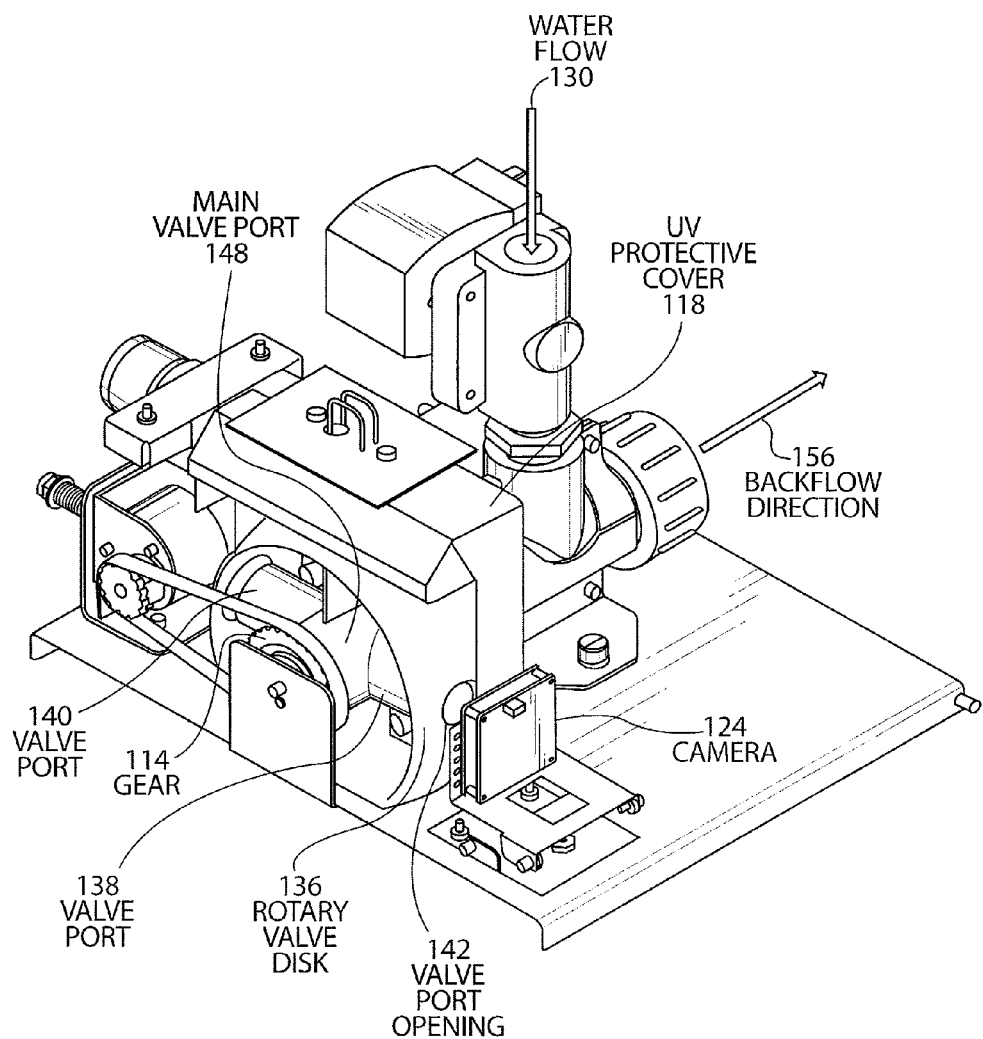
FIG. 2 is a schematic isometric rendering of the sanitary dispensing assembly of the embodiment of FIG. 1 with the UV protective cover removed.
Figure 3:
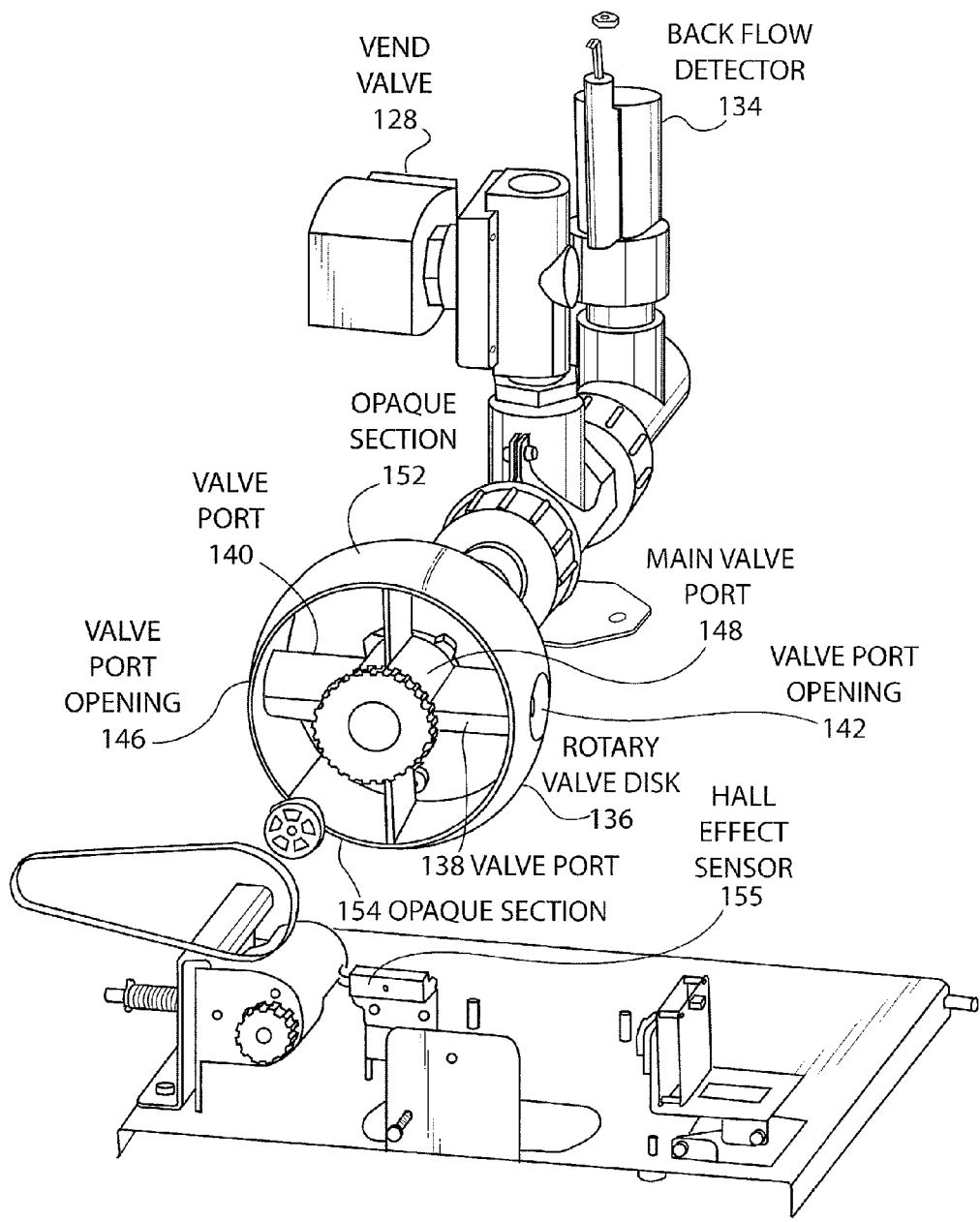
FIG. 3 is an exploded diagram illustrating portions of the embodiment of FIG. 1.

FIG. 2 is an isometric diagram of various parts of the embodiment of FIG. 1 with the UV protective cover 118 removed. As shown in FIG. 2, a rotary valve disk 136 is illustrated that has a main valve port 148 and two valve ports 138, 140 that extend from the main valve port 148. The main valve port 148 is coupled to a gear 114 that causes rotary valve disk 136 to rotate around the central axis of the main valve port 148. Valve port 138 is connected to valve port opening 142. Similarly, valve port 140 is connected to valve port opening 146 (FIG. 3). The rotary valve disk 136, as shown in FIG. 2, is in one of the two rest positions that are explained in more detail below. In the rest position shown in FIG. 2, camera 124 is aligned with the valve port opening 142 to inspect the valve port opening 142 and valve port 138 to ensure that there is no blockage or other problems with the valve port opening 142 or valve port 138. The inspection and analysis of the image of valve port opening 142 and valve port 138 that is created by camera 124 can be performed automatically by pattern recognition software. For example, each image created by camera 124 can be compared to a standard image of an unblocked valve port opening and unblock valve port. The digitized pixels can be compared using well known pattern recognition software to determine the difference between the current image and the standard image. If the difference is greater than a predetermined threshold, a signal may be sent to the main office to view the images from the camera 124 by a human to determine if blockage or other problems have occurred. This constitutes one method of pattern recognition, but many other methods exist that can be utilized to recognize whether a blockage or other problems exist in the valve port opening 142 and valve port 138.

Figure 4:
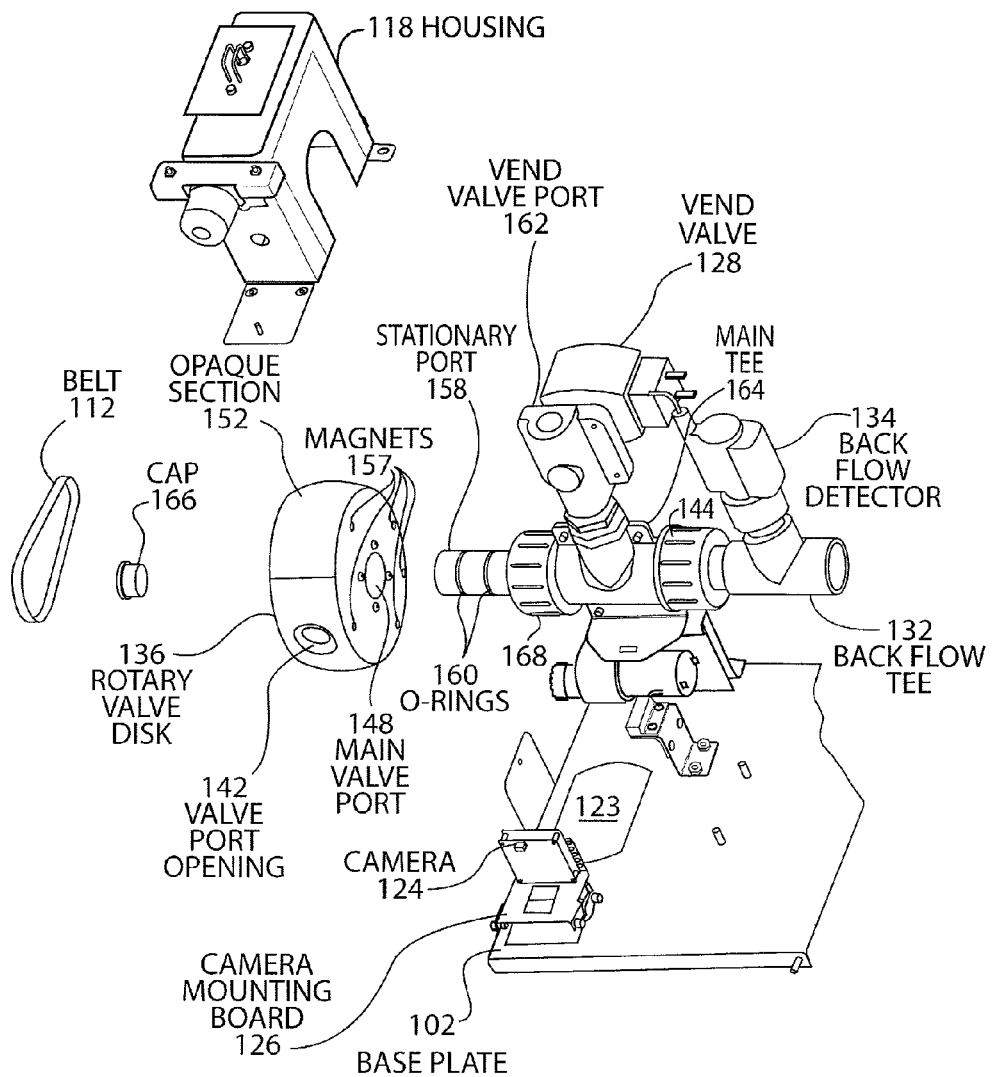
FIG. 4 is another exploded diagram illustrating portions of the embodiment of FIG. 1.
Figure 7:
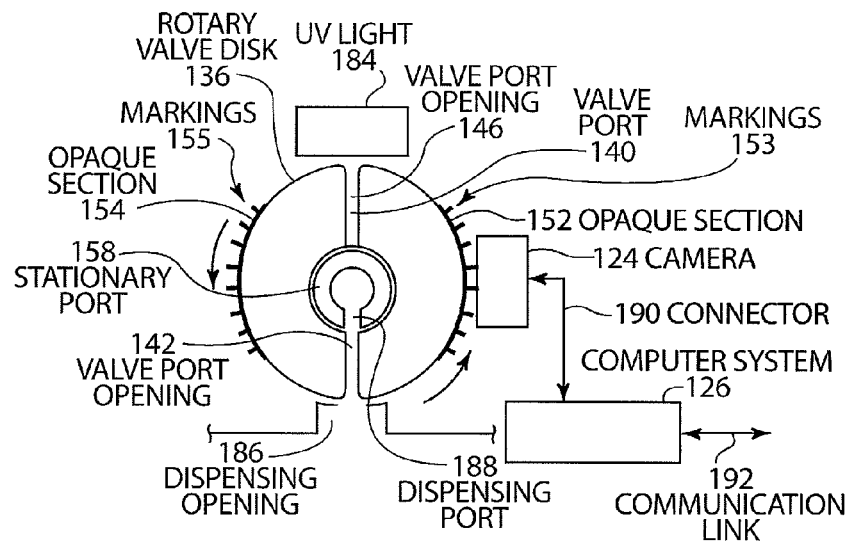
FIG. 7 is a schematic illustration showing the manner in which the rotary dispensing valve operates.

As also shown in FIG. 2, a UV protective cover 118 is illustrated that contains the UV light that radiates UV-C radiation in a downward direction over the rotary valve disk 136. The UV protective cover 118 helps to contain the UV-C radiation from the UV light 184 (FIG. 7). The UV light 184 may comprise a mercury vapor light that is capable of emitting high-intensity UV-C radiation that disinfects the outer surfaces of the rotary valve disk 136, including the valve port openings 142, 146 of the rotary valve disk 136. The UV-C radiation also illuminates the valve ports 138, 140 and disinfects the interior surfaces of the valve ports 138, 140. The intensity and frequency of the UV-C radiation is capable of killing viruses, bacteria and other microbes that may contact the outer surface of the rotary valve disk 136 from user containers, fingers, or by other means. In addition, the UV-C radiation can kill insects and other bugs that may crawl into the valve port openings 142, 146. FIG. 2 also illustrates the direction of water flow 130 in the vend valve port 162 (FIG. 4). If the main valve port 148, or the connecting valve ports 138, 140 are blocked, for any reason, water flows in the backflow direction, as illustrated in by arrow 156.

FIG. 3 is an exploded diagram illustrating various parts of the embodiment of FIG. 1. As shown in FIG. 3, the rotary valve disk 136 has valve ports 138, 140. Valve port 138 is coupled to the valve port opening 142. Similarly, valve port 140 is coupled to the valve port opening 146. The opaque sections 152, 154 are disposed on opposite sides, of and in between, the valve port openings 142, 146 on the outer surface of the rotary valve disk 136. The opaque sections 152, 154 can be separate layers adhered to the outer surface of the rotary valve disk 136, or can be molded into the plastic of the rotary valve disk 136. The opaque sections 152, 154 are opaque to the UV-C radiation so that the UV-C radiation is not transmitted through the rotary valve disk 136 in the rest position, i.e., when the valve ports 138, 140 are horizontal.

Magnets 157 (FIG. 4) are also placed around the rotary valve disk 136. Hall effect sensor 155 (FIG. 3) is used to detect the position of the rotary valve disk 136. Control board 120 (FIG. 1) controls the operation of the motor 104 (FIG. 1) to position the rotary valve disk 136 in the proper orientation, as disclosed below, in accordance with the signal detected by the hall effect sensor 155. FIG. 3 also illustrates the vend valve 128 and a backflow detector 134.

FIG. 4 is another exploded diagram illustrating various parts of the embodiment of FIG. 1. Base plate 102 has an opening 123 in which the rotary valve disk 136 protrudes. Camera 124 is mounted on the base plate 102 adjacent the opening 123 via camera mounting board 127. Opaque section 152 is included on, or as part of, the rotary valve disk 136. The main valve port 148 is also illustrated in the rotary valve disk 136. The main valve port 148 extends through the center portion of the rotary valve disk 136. The main valve port 148 fits over the stationary port 158. O-rings 160 form a watertight seal between the inner surface of the main valve port 148 and the portion of the stationary port 158 between the O-rings 160. On the bottom portion of the stationary port 158, between the O-rings 160, is a dispensing port 188 (FIG. 5) through which water flows from the center part of the stationary port 158. When the valve ports 138, 140 (FIG. 3) of the rotary valve disk 136 are aligned with the opening at the bottom of the stationary port 158, water can flow through the valve ports 138, 140 and rotary disk 136. Stationary port 158 remains stationary and does not rotate. The rotary valve disk 136 rotates on the stationary port 158. Cap 166 attaches with a screw to stationary port 158 and holds the rotary valve disk 136 on the stationary port 158. The stationary port 158 is coupled to the main Tee 164 with a compression fitting 168. Vend valve port 162 is connected to the center port of the main Tee 164 where water flows downward through the vend valve port 162 when the vend valve 128 is activated to open in response to user interaction such as placing money in the dispensing machine. The other portion of the main Tee 164 is connected to a backflow Tee 132 using another compression fitting 144. A backflow detector 134 is connected to the center port of the backflow Tee 132. The backflow detector 134 generates a signal whenever water flows through the backflow Tee 132. The belt 112 and UV protective cover 118 are also shown in the exploded diagram of FIG. 4.

Figure 5:
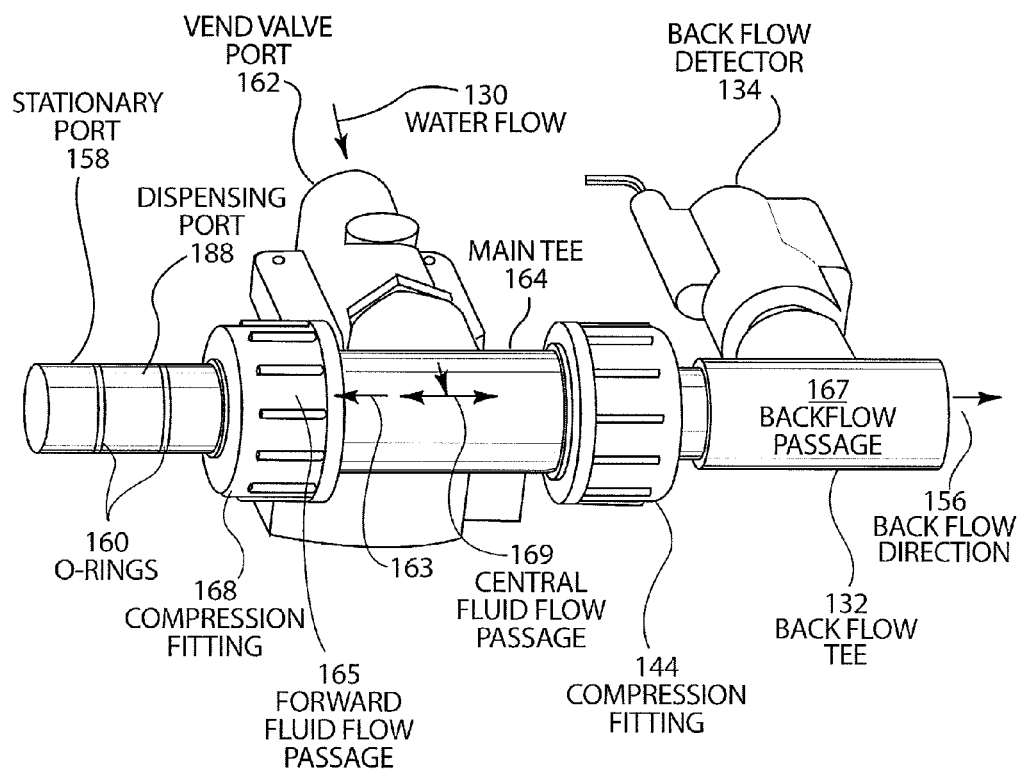
FIG. 5 is isometric diagram illustrating portions of the embodiment of FIG. 1.

FIG. 5 is a schematic isometric diagram illustrating various portions of the embodiment of FIG. 1. As shown in FIG. 5, the stationary port 158 has a dispensing port 188 at the bottom of the stationary port 158. The dispensing port 188 is located between the O-rings 160 which seal with the surface of the main valve port 148 so that water is directed through the dispensing port 188 and through the valve ports 138, 140 (FIG. 3) when the valve ports 138, 140 are aligned with the dispensing port 188. As also shown in FIG. 5, the vend valve port 162 is connected to the main Tee 164. Stationary port 158 is connected to the main Tee 164 by compression fitting 168. Similarly, backflow Tee 132 is connected to the main Tee 164 by compression fitting 144. As also illustrated in FIG. 5, the back flow detector 134 is connected to the center port of the backflow Tee 132. FIG. 5 also illustrates the direction 130 of water flow through the vend valve port 162. Water flows through the vend valve port 162 to the main Tee 164. The vend valve port 162 and main Tee 164 comprise a central fluid flow passage 169. The water can either flow in a forward direction 163 in a forward fluid flow passage 165 or in a back flow direction 156 through a backflow passage 167 through the back flow Tee 132.

Figure 6A:
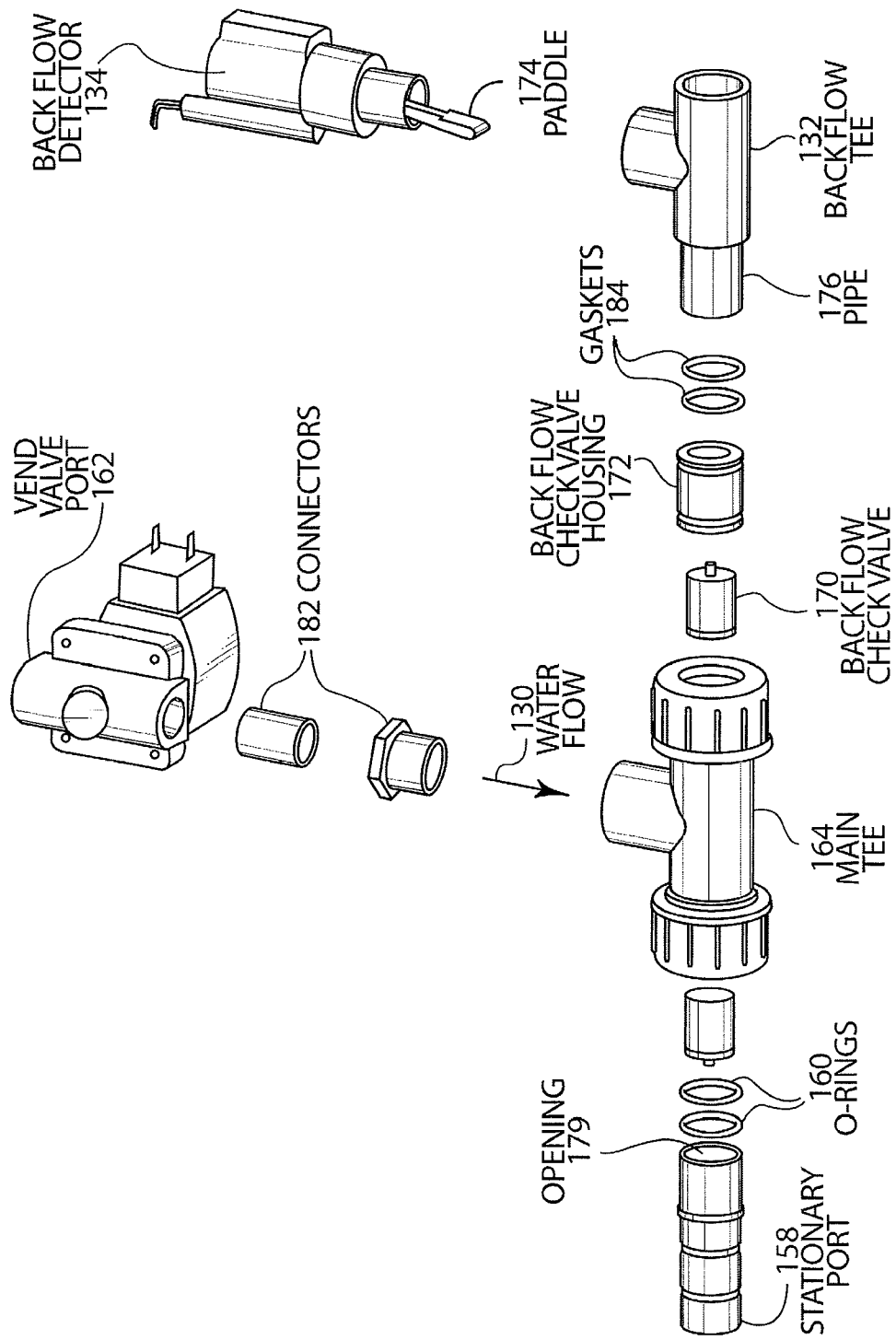
FIG. 6 is an exploded diagram illustrating portions of the embodiment of FIG. 1.

FIG. 6A is an exploded diagram illustrating various parts of the embodiment of FIG. 1. As shown in FIG. 6A, the stationary port 158 is fitted with O-rings 160 that seal against the inner surface of the main valve port 148 (FIG. 4). As also shown in FIG. 6, the vend valve port 162 is connected by connectors 182 to the main Tee 164. Water flows in the central fluid flow passage 169 (FIG. 5) through the vend valve port 162, connectors 182 and main Tee 164 in the direction of the arrow 130.

Figure 6B:
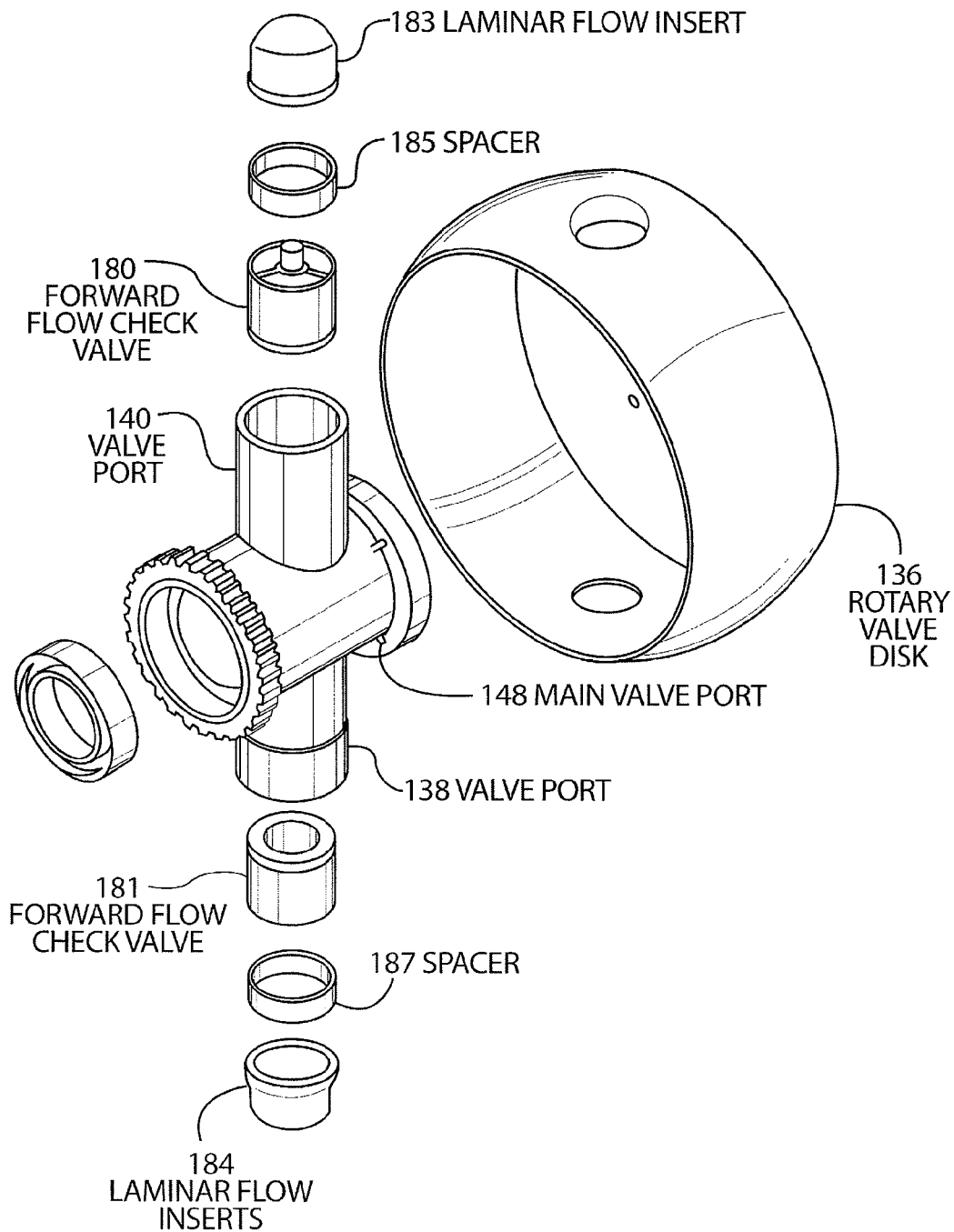

FIG. 6B is an exploded diagram illustrating the rotary valve disk 136, the structure comprising the main valve port 148, valve port 140, valve port 138 and various associated parts. As shown in FIG. 6B, forward flow check valve 180 is disposed in valve port 140, while forward flow check valve 181 is disposed in valve port 138. Spacer 185 separates the forward flow check valve 180 from a laminar flow insert 183 that are also inserted in the valve port 140. Similarly, spacer 187 separates the forward flow check valve 181 from the laminar flow insert 184 which are inserted in the valve port 138. The forward flow check valves 180, 181 cut off the flow of water to the dispensing opening 186 (FIG. 7) whenever the pressure of the water drops below a predetermined amount. This is normally in the range of only a few pounds per square inch of water pressure. The forward flow check valves 180, 181 prevent the dribbling of water out of the dispensing opening 186 when the dispensing cycle is completed. In other words, the forward flow check valves 180, 181 cut off the flow of water in the valve ports 140, 138, respectively, so that there is a minimal amount of water that can dribble from the dispensing opening 186 when the flow of pressurized water stops at the end of the vend cycle. Since the forward flow check valve 180 and the forward check valve 181 are located in the valve ports 140, 138, respectively, there is no passage way for the water to be stored and dribble through the dispensing opening 186 at the end of the vend cycle. As a result, the forward flow check valves 180, 181 do not allow water to be stored in any passage way that can be accessed by a user or that is open to the environment which could become contaminated.

Referring again to FIG. 6A, a backflow check valve 170 is mounted in a backflow check valve housing 172 which is inserted in the pipe 176 with gaskets 184. The backflow check valve 170 allows water to flow through the pipe 176 and backflow Tee 132 to a drain if the pressure on the backflow check valve 170 exceeds a predetermined amount. The predetermined amount of pressure of the backflow check valve 170 is substantially higher than the predetermined amount of pressure for the forward flow check valves 180, 181. In that regard, water flows through in the forward direction through the forward fluid flow passage 165 (FIG. 5) through forward flow check valves 180, 181 as long as the pressure exceeds a low pressure, such as one or several pounds per square inch. However, if the water pressure in the central fluid flow passage 169 exceeds approximately 5 or 10 pounds per square inch, water flows through the backflow passage through check valve 170 and the backflow Tee 132 to a drain. When the water pressure in the main Tee 164 exceeds 5 or 10 pounds per square inch, it is an indication that the forward flow of water has been blocked in some fashion, such as by tampering or misoperation of the rotary valve disk 136. When water begins to flow through the backflow Tee 132, the paddle 174 of the backflow detector 134 moves which causes the backflow detector 134 to generate a detection signal indicating that water is flowing through the backflow. A signal is generated in the water dispensing system that is communicated to the central office so that the camera can check for blockage in the valve ports. The dispensing system can be operated and viewed remotely through use of encoded signals over the Internet or a virtual private network. For example, encoded signals can be sent to operate the rotary valve disk 136 to determine if the rotary valve disk 136 is operating, which can be determined by sensing the signals from the hall effect sensor 155. If there is a blockage in the valve ports 138, 140, as indicated by the camera 124, or the rotary valve disk 136 does not rotate, as indicated by the hall effect sensor 155, or by viewing the camera 124, a service technician can be called to service the unit.

FIG. 7 is a schematic diagram illustrating the manner in which the rotary valve disk 136 operates to dispense water. FIG. 7 is a schematic cutaway view of the rotary valve disk 136 and the stationary port 158. FIG. 7 illustrates the rotary valve disk 136 in a dispense position. Water flows through the central opening in the stationary port 158 through the dispensing port 188 of the stationary port 158, through the valve port 142 that is aligned with the dispensing port 188 and through the dispensing opening 186 to the user. As shown in FIG. 7, the UV light 184 irradiates the valve port opening 146 in the valve port 140 to kill any microbes from the previous vend. This occurs while water is being dispensed through valve port 142 so that there is no delay involved in the process of disinfection. The opaque sections 152, 154 are aligned along the sides of the rotary valve disk 136 while the rotary valve 136 is in one of the two dispensing orientations, as illustrated in FIG. 7. Camera 124 is aligned with an opaque section and can simply view the opaque portion of the rotary valve disk 136. The opaque portions 152, 154 can be encoded with information such as makings 153, 155 indicating which opaque section is aligned with the camera 124 and provide centering data to allow a viewer of the camera image to determine if the rotary valve disk 136 is properly aligned to dispense water. Camera 124 is coupled to the on-board computer system 126 via connector 190. Communications link 192 connects the on-board computer system 126 to the central office and/or a regional maintenance station so that images can be transmitted to the central office/regional maintenance station for viewing and software operations can be performed remotely.

Figure 8:
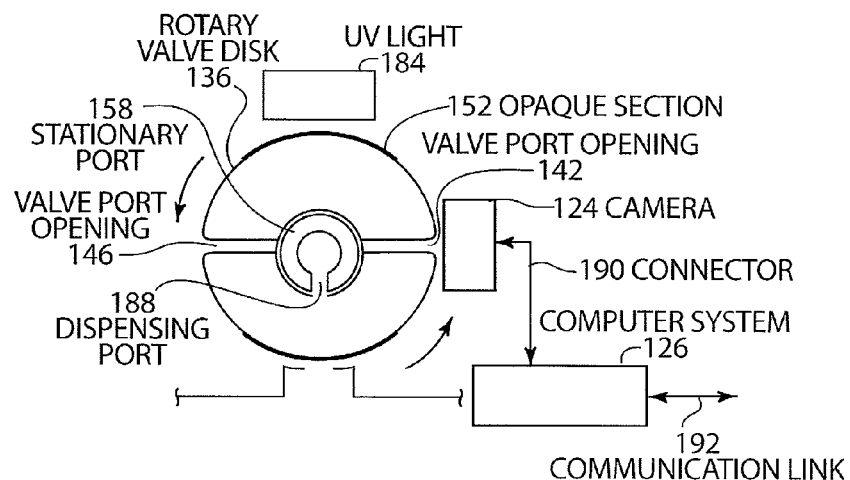
FIG. 8 is another schematic diagram illustrating the manner in which the rotary dispensing valve operates.

FIG. 8 is a schematic diagram of the rotary valve disk 136 in a first rest position. As shown in FIG. 8, the rotary valve disk 136 has rotated 90 degrees from the position in FIG. 7 in a counterclockwise direction. The valve port opening 146 that has been disinfected by the UV light 184 is now in a position on the left horizontal side of the rotary valve disk 136. The UV light 184 is aligned with the opaque section 152 and does not transmit any light through the rotary valve disk 136. The dispensing port 188 in stationary port 158 is aligned with a flat section of the interior surface of the main valve port 148 (FIG. 4). Hence, if water is dispensed while the rotary valve disk 136 is in this position, water will not flow from the dispensing port 188, but rather, create a back pressure that exceeds the backflow pressure of the backflow check valve 172, which causes the water to flow in the backflow direction to a drain. In that case, the backflow detector 134 (FIG. 6) generates a signal indicating that water is flowing in the backflow direction. The camera 124 can then be activated to determine the orientation of the rotary valve disk 136 and the image can be transmitted via connector 190 to computer system 126 for transmission to a central office and/or regional maintenance office via link 192. As described above, camera 124 can generate an image of the valve port opening 142 and perform pattern recognition techniques to determine if there is a blockage in the valve port opening 142 so that an alarm can be generated and an image transmitted to a central office or regional maintenance office.

Figure 9:
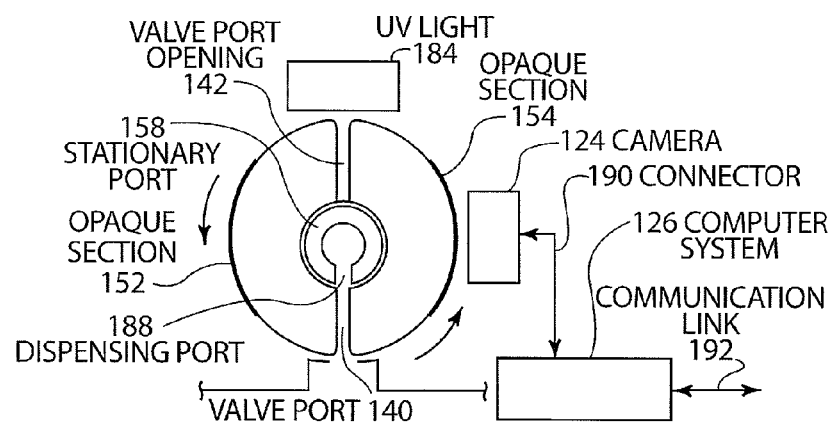
FIG. 9 is another schematic diagram illustrating the manner in which the rotary dispensing valve operates.

FIG. 9 is a schematic illustration of the rotary valve disk 136 that is rotated another 90 degrees in a counterclockwise direction from the position of the rotary valve disk 136 in FIG. 8. As shown in FIG. 9, the valve port opening 142 is aligned with the UV light 184 so that the valve port opening 142 is disinfected with the UV-C radiation from the UV light 184 during a vend operation. The dispensing port 188 of the stationary port 158 is aligned with the valve port 140 to dispense water through the dispenser opening 186. The opaque sections 152, 154 are aligned with the sides of the rotary valve disk 136 in the orientation illustrated in FIG. 9. Camera 124 is aligned with opaque section 154. Location and centering information 153, 155 can be provided on the opaque sections 152, 154 so that the camera 124 can generate an image to determine if the rotary valve disk 136 is in the proper orientation. This image can be transmitted through connector 190 to the on-board computer 126 and through a communications link 192 to the central office and/or a regional maintenance office. Connector 190 and communications link 192 can also transmit control signals that control the operation of the camera 124. The rotary disk then continues to rotate in a counter clockwise direction by 90 degrees and the cycles described above are repeated for these additional orientations of the rotary valve disk 136.

Figure 10:
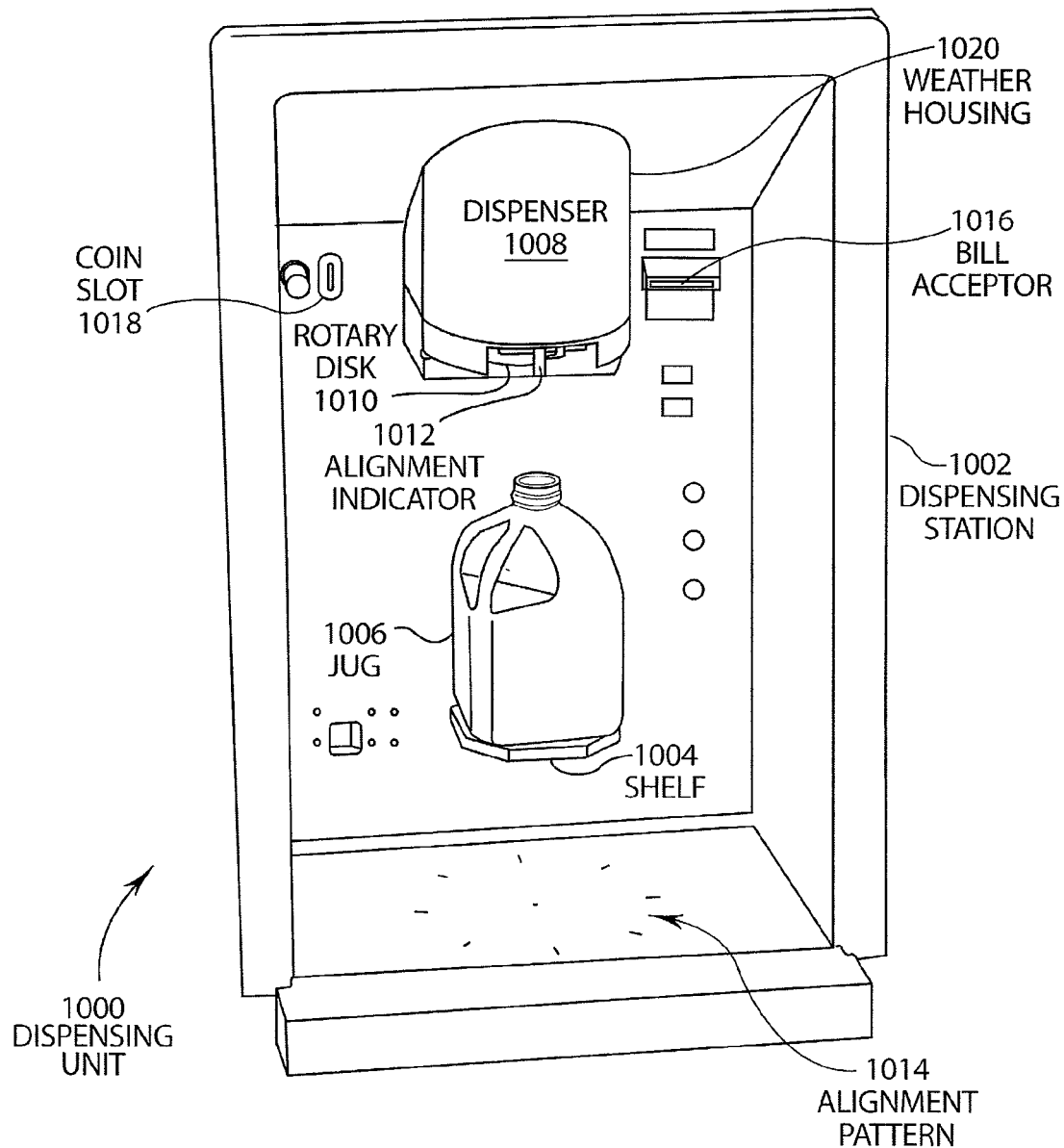
FIG. 10 is an isometric diagram of the public access portion of another embodiment of a dispenser unit.
Figure 11:
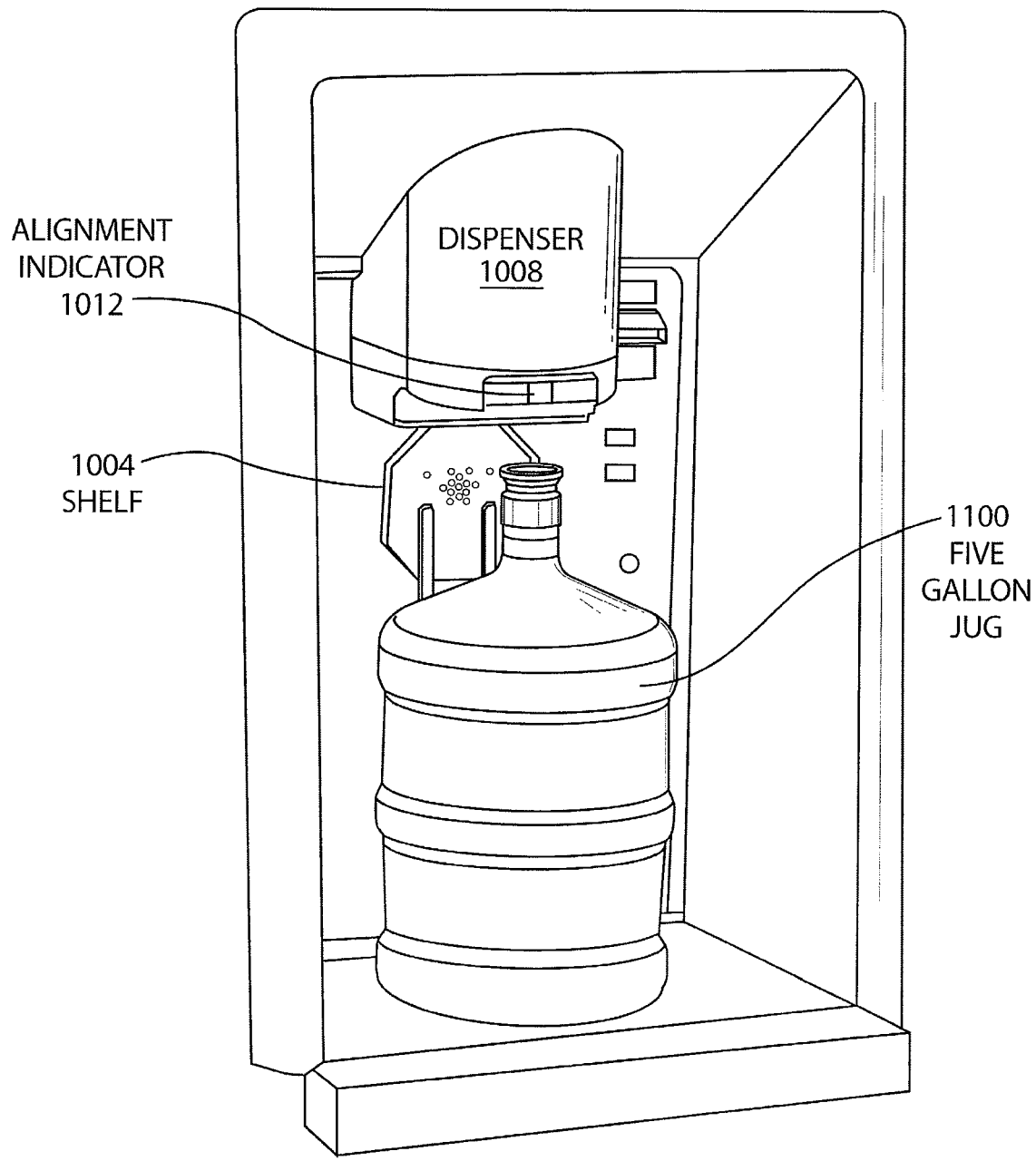
FIG. 11 is another view of the embodiment of FIG. 10.

FIG. 10 is an illustration of another embodiment of a dispenser device. This embodiment can be incorporated in a walk-up or drive-up kiosk or can be mounted in a wall or other structure for dispensing water. This embodiment, as well as the embodiment of FIGS. 1-9 can also be used in movable or portable systems that can be located in different places. As shown in FIG. 10, the dispenser 1008 is located in the opening of the dispenser unit 1000 that includes a tray having an alignment pattern 1014 for aligning a bottle, such as a five gallon bottle, such as illustrated in FIG. 11. In addition, the dispensing unit 1000 has a shelf 1004 for placement of jugs, such as a gallon jug 1006. The dispensing unit 1000 also has a bill accepter 1016 and a coin slot 1018 that accept money for payment to dispense water. The dispenser 1008 has a weather housing 1020 that protects the dispenser 1008 from weather and tampering. The weather housing 1020 may be made of a stainless steel material that provides an aesthetic appearance and prevents tampering. Rotary disk 1010 forms a portion of the dispenser 1008. The rotary disk 1010 is made of a clear plastic material and includes an alignment indicator 1012 that comprises a solid cylinder. The alignment indicator 1012 is visible through the clear plastic of the rotary disk 1010 and assists the user in aligning containers, such as jug 1006, with the flow of water. In that regard, the alignment indicator 1012 is positioned in the same location as a vend port 1306 (FIG. 13) when water is dispensed from the dispenser 1008. The alignment indicator 1012 has the same shape and size as a vend port, such as vend port 1306, so that a user of the dispenser unit 1000 can adequately align a container, such as jug 1006, with the flow of water. Rotary disk 1010 may be illuminated with one or more lights, such as blue lights, that allow the alignment indicator 1012 to be easily located by the user. In addition, the blue lights that illuminate the rotary disk 1010 provide a pleasing and clean appearance, together with the stainless steel covering of the weather shielding 1020 that provides an image of a clean, high-tech apparatus for providing water to users. The rotary disk 1010, as disclosed in more detail below, prevents vandals from tampering with the system by providing a physical barrier to would-be vandals from accessing the interior of the dispensing unit 1000.

FIG. 11 is another illustration of the embodiment of FIG. 10. As shown in FIG. 11, a five gallon jug 1100 is used with the dispensing unit 1000, and is placed on the alignment pattern 1014 that is illustrated in FIG. 10. In addition, the neck of the five gallon jug 1100 can be visually aligned with the alignment indicator 1012 to ensure that water is dispensed directly into the five gallon jug 1100 without spillage. The shelf 1004 is folded or retracted into a recessed position, so that the five gallon jug 1100 can fit into the dispensing unit 1000. Shelf 1004 may be spring-loaded or have a counterweight to ensure that the shelf 1004 normally remains in the folded position, as shown in FIG. 11.

Figure 12:
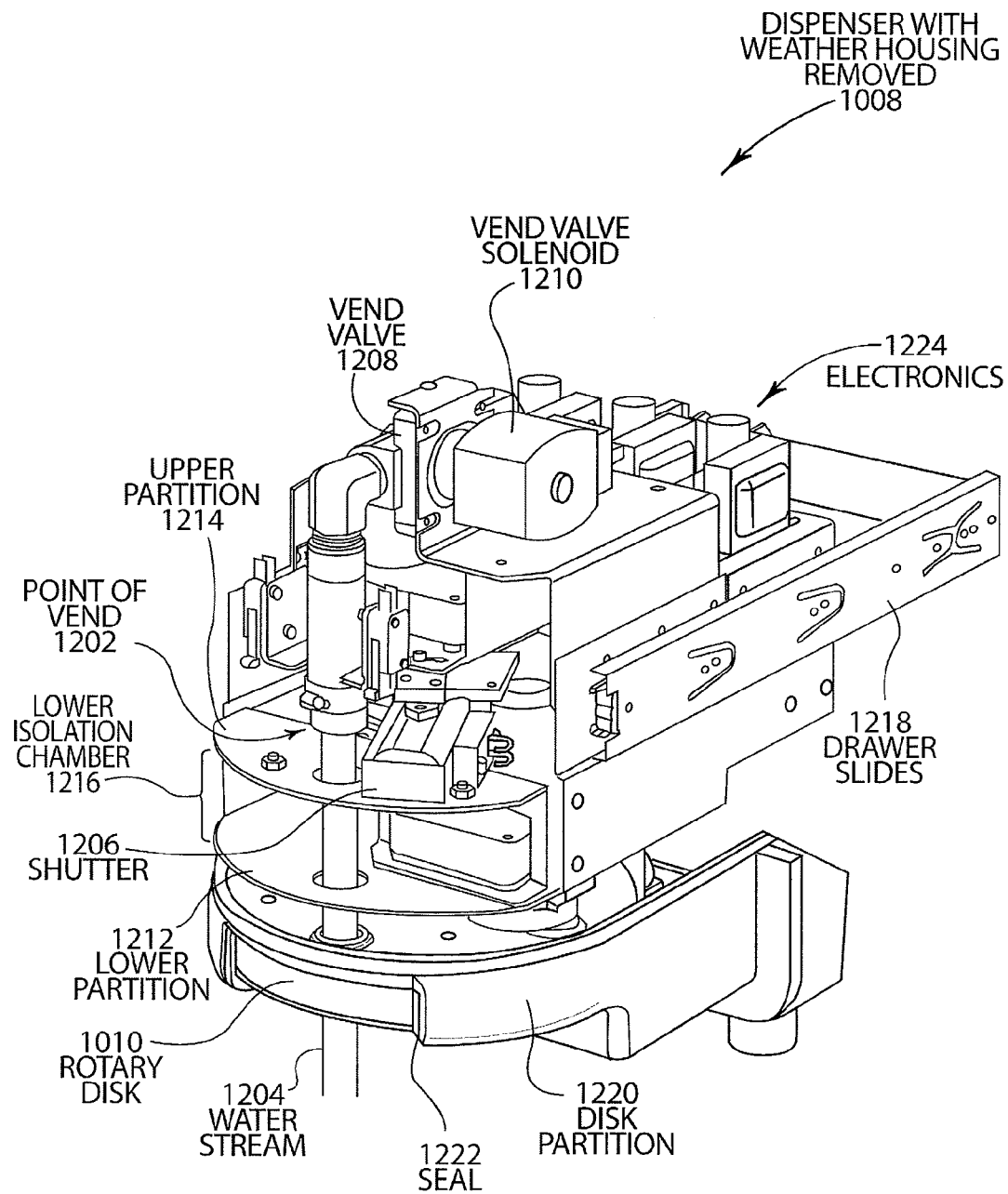
FIG. 12 is an isometric diagram of the embodiment of the dispenser of FIG. 11 with the weather housing removed.
Figure 32:
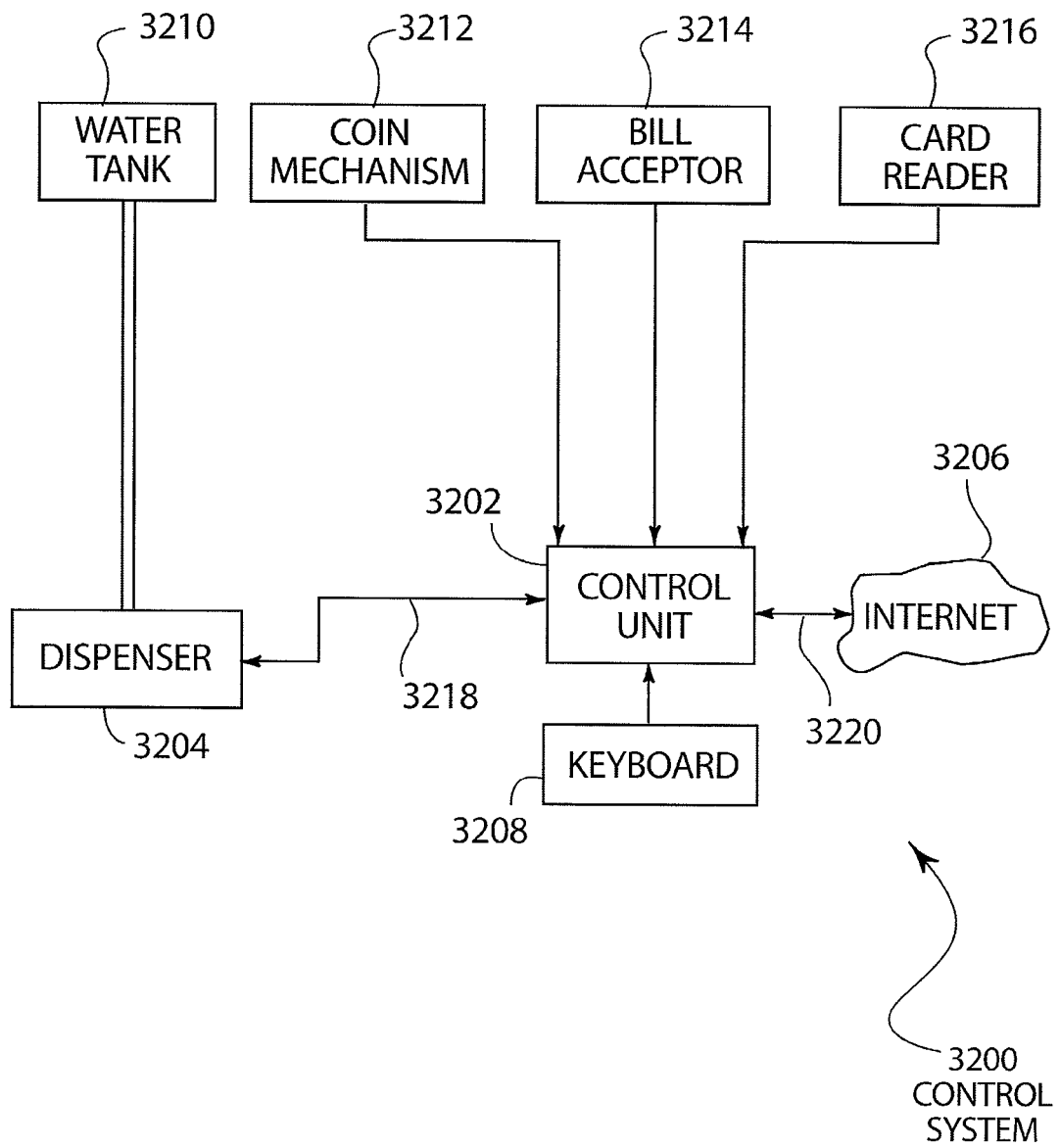
FIG. 32 is a schematic block diagram of the electronic control circuit.

FIG. 12 is an isometric view of the dispenser 1008 with the weather housing removed. As shown in FIG. 12, the dispenser 1008 is mounted on drawer slides 1218 that allow the dispenser 1008 to be pulled in a rearward direction for service. Dispenser 1008 includes electronics 1224 that operate various servo systems and UV lights, as well as drive various types of motors, under the control of a computer control system 3200 (FIG. 32). As indicated above, the rotary disk 1010 provides a first physical barrier to prevent access to the interior portion of the dispenser 1008. Lower partition 1212 and upper partition 1214 comprise a second and third barrier layer and also form a lower isolation chamber 1216. When water is not being dispensed via water stream 1204, shutter 1206 is in the open or vend position, as shown in FIG. 12. However, as disclosed below, when the dispenser 1008 is in the idle position, the shutter 1206 is rotated to cover the opening in the upper partition 1214 and isolate the lower isolation chamber 1216 from the remaining upper portions of the dispenser 1008. The remaining upper portions of the dispenser 1008 include the point of vend 1202, that is the point at which the water stream is dispensed. This occurs in response to activation of the vend valve solenoid 1210 that is coupled to the vend valve 1208 that controls the flow of water. FIG. 12 also illustrates the disk partition 1220 that provides another physical barrier to prevent vandals from accessing the dispenser 1008. Seal 1222 provides a seal around the rotary disk 1010 that prevents external elements, such as dust and moisture, from entering the dispenser 1008.

Figure 13:
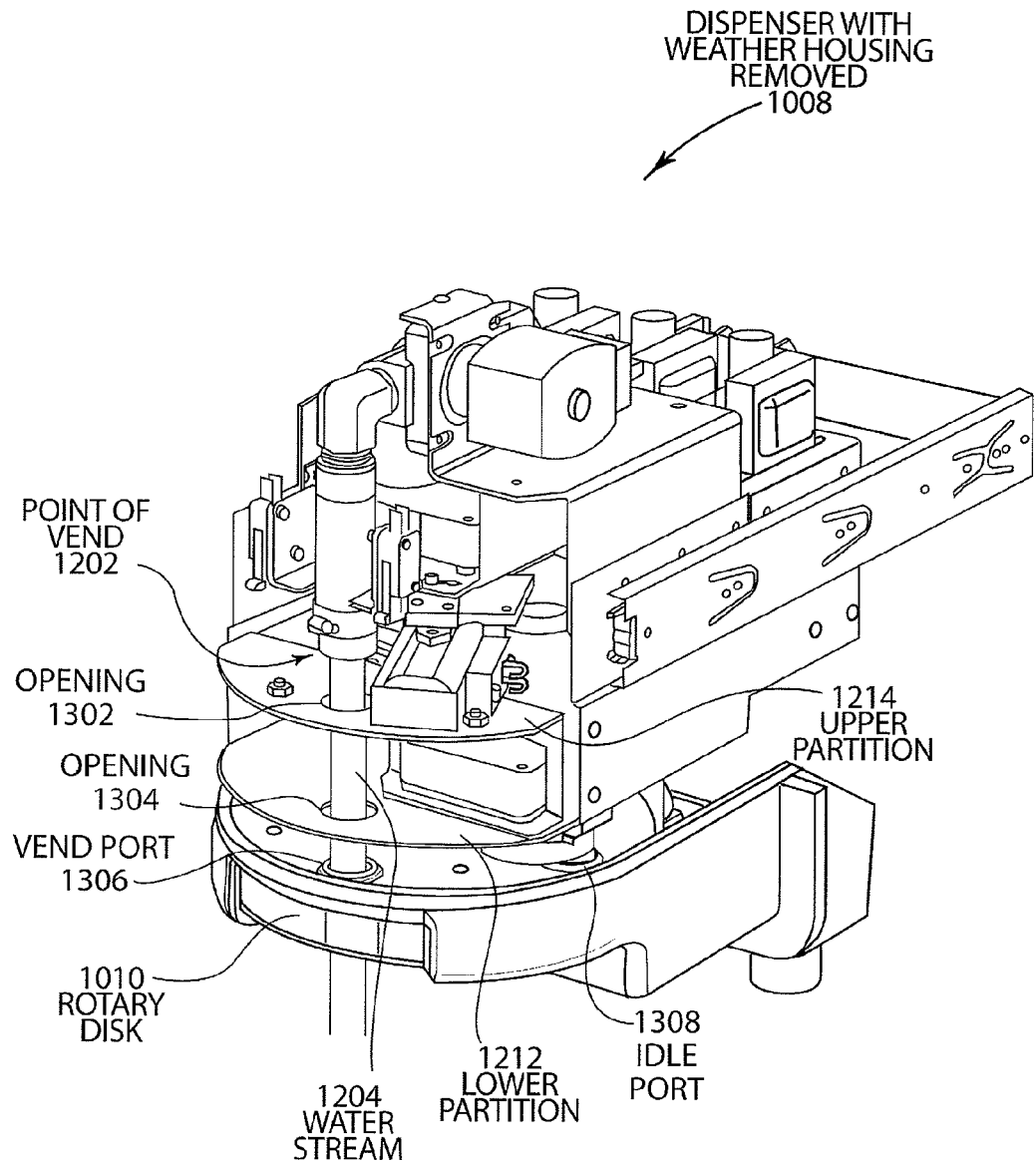
FIG. 13 is another isometric diagram of the dispenser of FIG. 11 with the weather housing removed.

FIG. 13 is another view of the dispenser 1008 with the weather housing removed. As shown in FIG. 13, the point of vend 1202 is aligned with the opening 1302 in the upper partition 1214. In addition, opening 1304 in the lower partition 1212 is also aligned with the water stream 1204. The water stream 1204 then proceeds downwardly through the vend port 1306 that is formed in the rotary disk 1010. In this manner, water is dispensed to the user through the various openings 1302, 1304 and vend port 1306.

Figure 14:
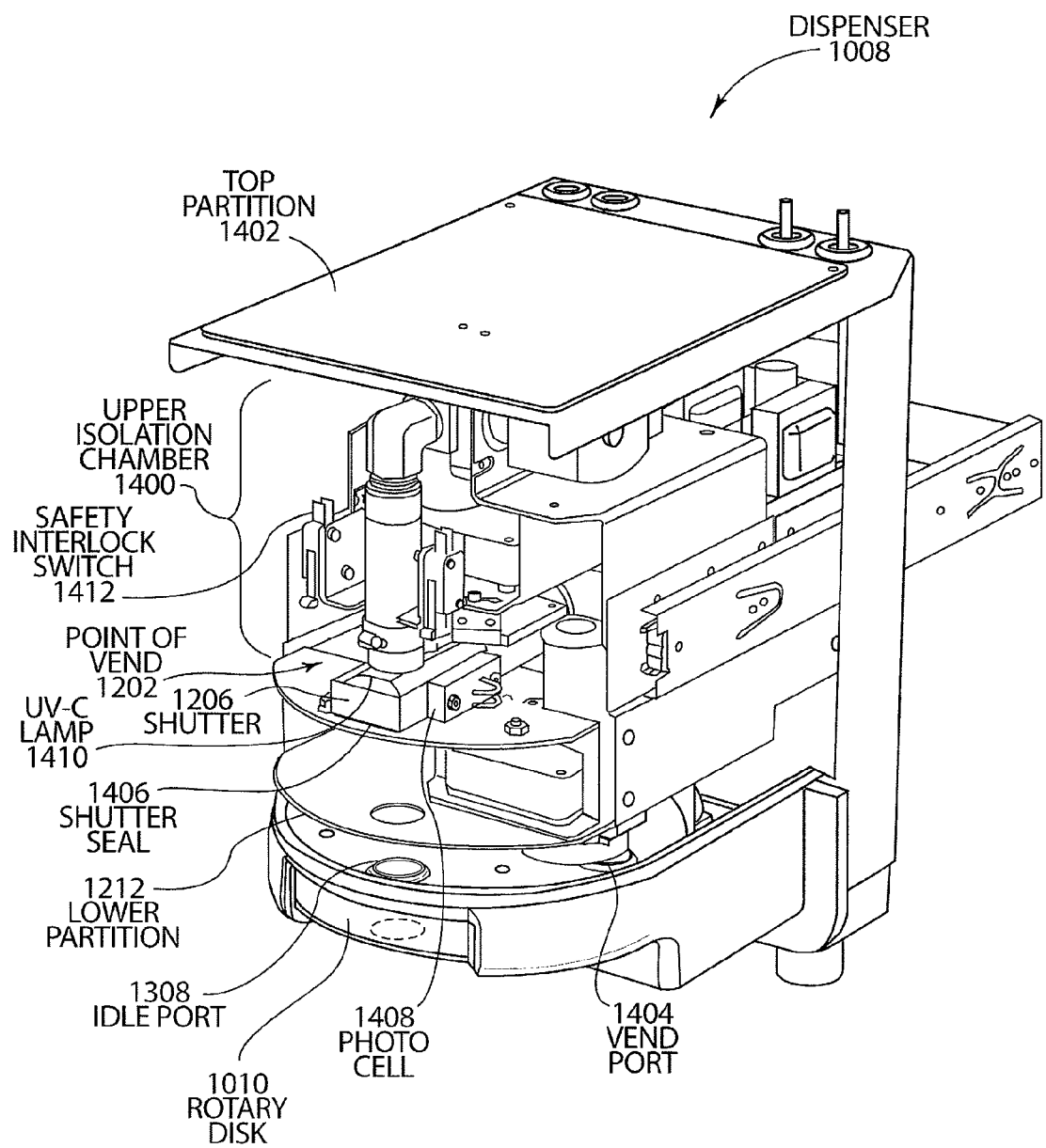
FIG. 14 is another isometric diagram of the embodiment of the dispenser of FIG. 11 with the weather housing removed.

FIG. 14 is another view of the dispenser 1008 with the weather housing removed. As shown in FIG. 14, a top partition 1402 and the lower partition 1212 form an upper isolation chamber 1400. As shown in FIG. 14, the rotary disk 1010 is rotated to the idle position, so that the idle port 1308 is aligned with the point of vend 1202 when the dispenser 1008 is in the idle position. In the idle position, the rotary disk 1010 and the idle port 1308 provide a physical barrier to prevent vandals from accessing the interior portion of the dispenser 1008. The vend port 1404, as illustrated in FIG. 14, is in the vend position and is not aligned with the point of vend 1202. In the idle position, as shown in FIG. 14, the shutter 1206 is moved to a position directly under the point of vend 1202 and seals the opening 1302 (FIG. 13) to prevent access to the upper isolation chamber 1400. Shutter 1206 includes a shutter seal 1406 that seals off weather and dust from the upper isolation chamber 1400. UV-C lamp 1410 is aligned with the bottom portion of the point of vend 1202 when the shutter 1206 is in the idle position, as illustrated in FIG. 14. Prior to dispensing water, the UV-C lamp 1410 irradiates the opening in the point of vend 1202 to disinfect and kill any germs that may exist on the opening in the point of vend 1202. Photocell 1408 determines if the UV-C lamp 1410 is operating. If the photocell 1408 does not detect radiation from the UV-C lamp 1410, a signal will be generated and an error message will be sent from the dispenser unit 1008 to the home office via the Internet, as more fully disclosed with respect to FIG. 32.

Figure 15:
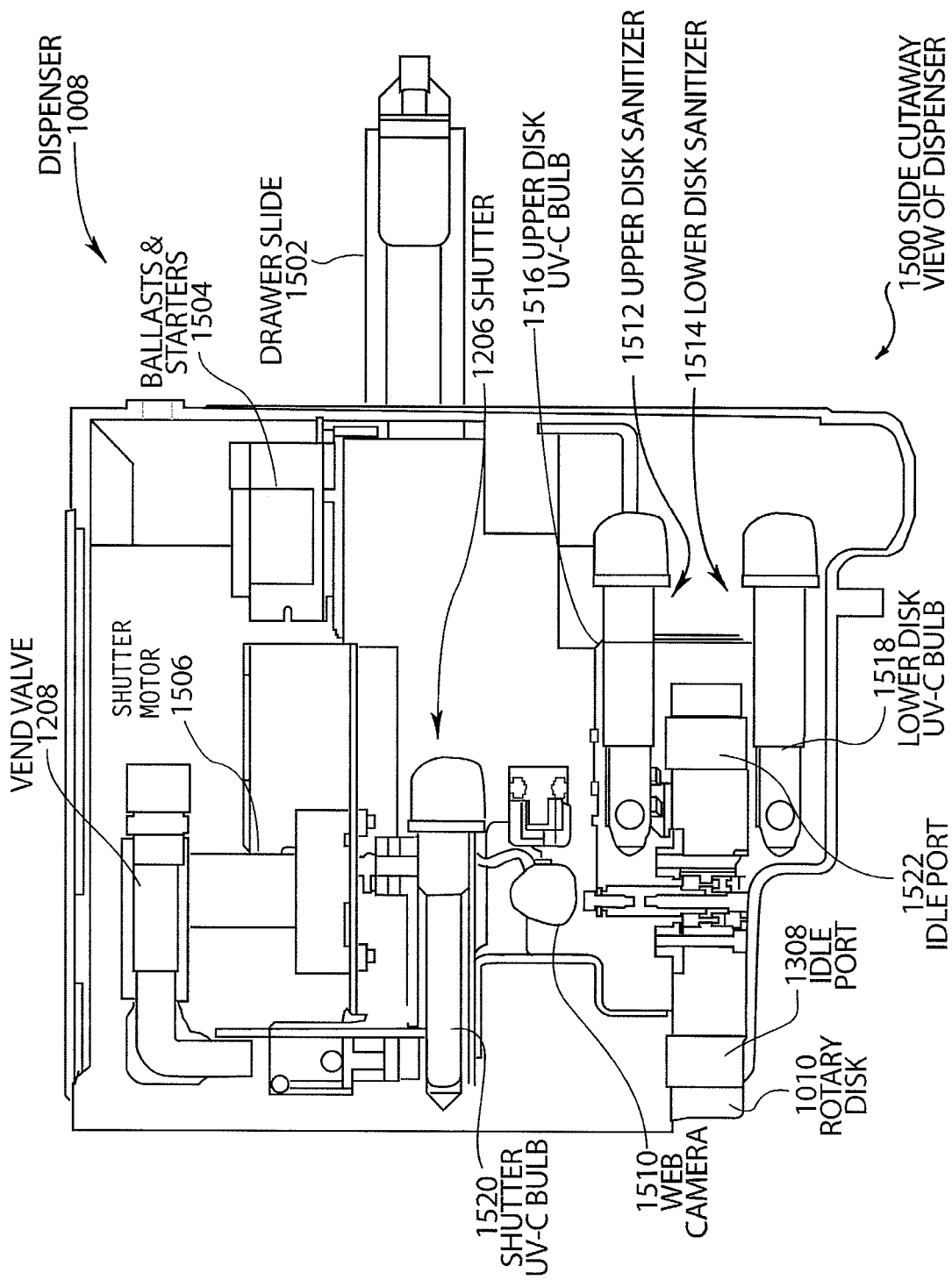
FIG. 15 is a side cutaway view of the embodiment of the dispenser of FIG. 11.

FIG. 15 is a side view 1500 of the dispenser 1008 with the weather housing 1020 removed. As shown in FIG. 15, rotary disk 1010 is in the idle position, such that the idle port 1308 is aligned with the shutter 1206 that is in the closed or idle position. FIG. 15 illustrates the upper disk sanitizer 1512, that is located above the rotary disk 1010, and the lower disk sanitizer 1514, that is located below the rotary disk 1010. The upper disk sanitizer 1512 has an upper disk UV-C bulb 1516 that sanitizes the upper surface of the rotary disk 1010 and the openings in the vend ports 1306, 1404. The lower disk sanitizer 1514 has a lower disk UV-C bulb 1518 that sanitizes the lower surface of the rotary disk 1010 and the opening in the vend ports 1306, 1404. A web camera 1510 inspects for blockages or other problems that may exist in the dispenser 1008. The web camera 1510 is located above one of the vend ports when the rotary disk 1010 is located in the idle position, such as shown in FIG. 15. The web camera 1510 can send images to a central office whenever a problem is detected in the system. FIG. 15 also illustrates the drawer slide 1502 for moving the dispenser 1008 into a service position. Ballast and starters 1504 comprise a portion of the electronics 1224 (FIG. 12) that assist in operating the UV lamps, illustrated in FIG. 15. Shutter motor 1506 operates the shutter 1206 to move the shutter 1206 between a closed, idle position and an opened, vend position. A vend valve 1208 controls the dispensing of water.

Figure 16:
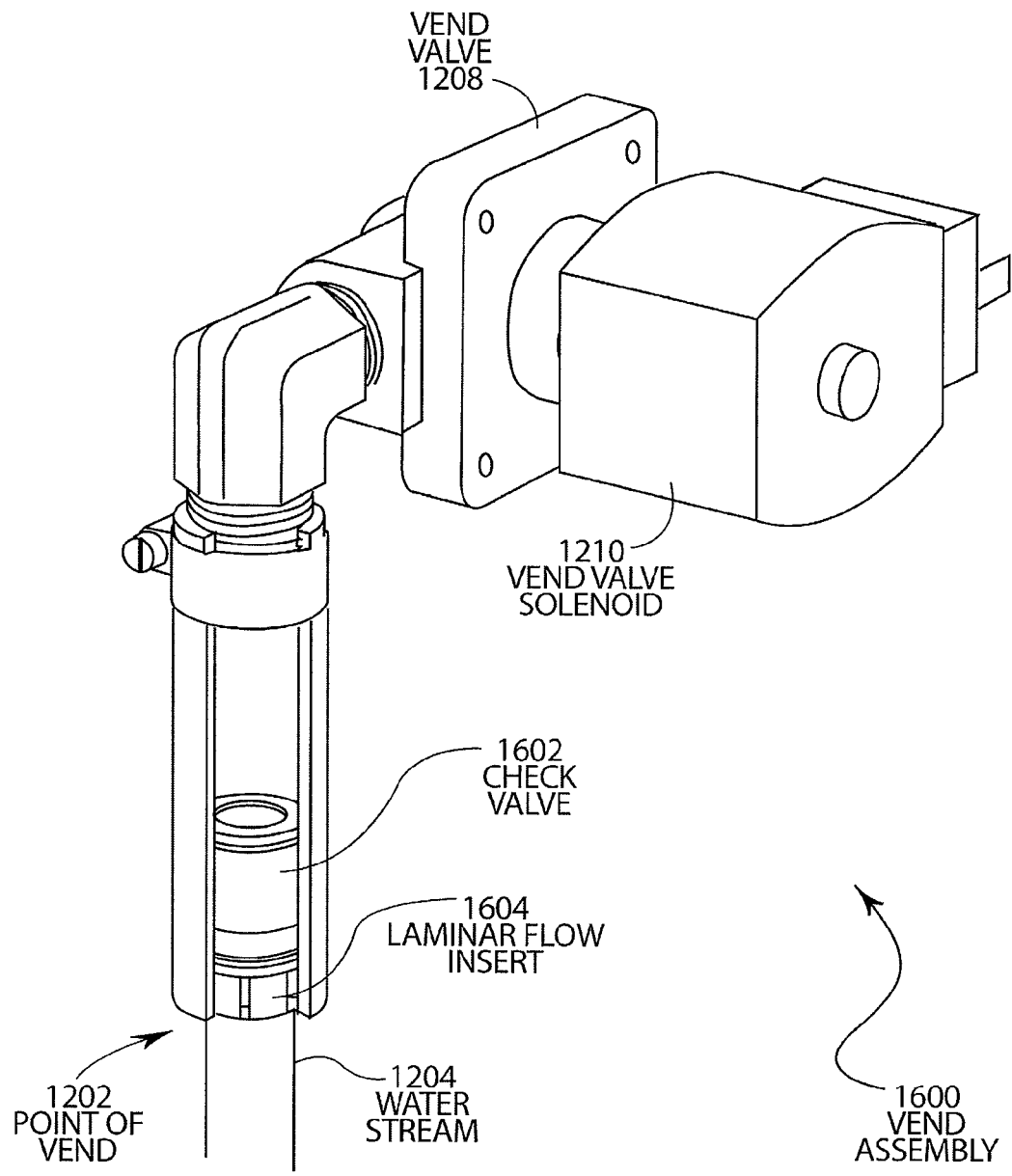
FIG. 16 is an isometric diagram of an embodiment of a vend assembly.

FIG. 16 is an isometric diagram of one embodiment of a vend assembly 1600. As shown in FIG. 16, the vend assembly 1600 includes the vend valve solenoid 1210, which is operatively coupled to the vend valve 1208. The vend valve solenoid 1210 is electrically connected to the control system 3200 (FIG. 32) of a dispenser 1008 and functions to open and close the vend valve 1208 in response to control signals. A check valve 1602 is located near the point of vend 1202. Check valve 1602 operates by opening when a predetermined amount of fluid pressure is applied to the check valve 1602. When the pressure drops, the check valve 1602 closes. Since the check valve 1602 is located near the point of vend 1202, the flow of water ceases nearly instantaneously and there is minimal dribbling after the vend process is completed. Laminar flow insert 1604 generates a laminar flow of water that prevents waste and provides a defined water stream 1204 that assists in collecting the water and aligning a jug with the defined water stream 1204.

Figure 17:
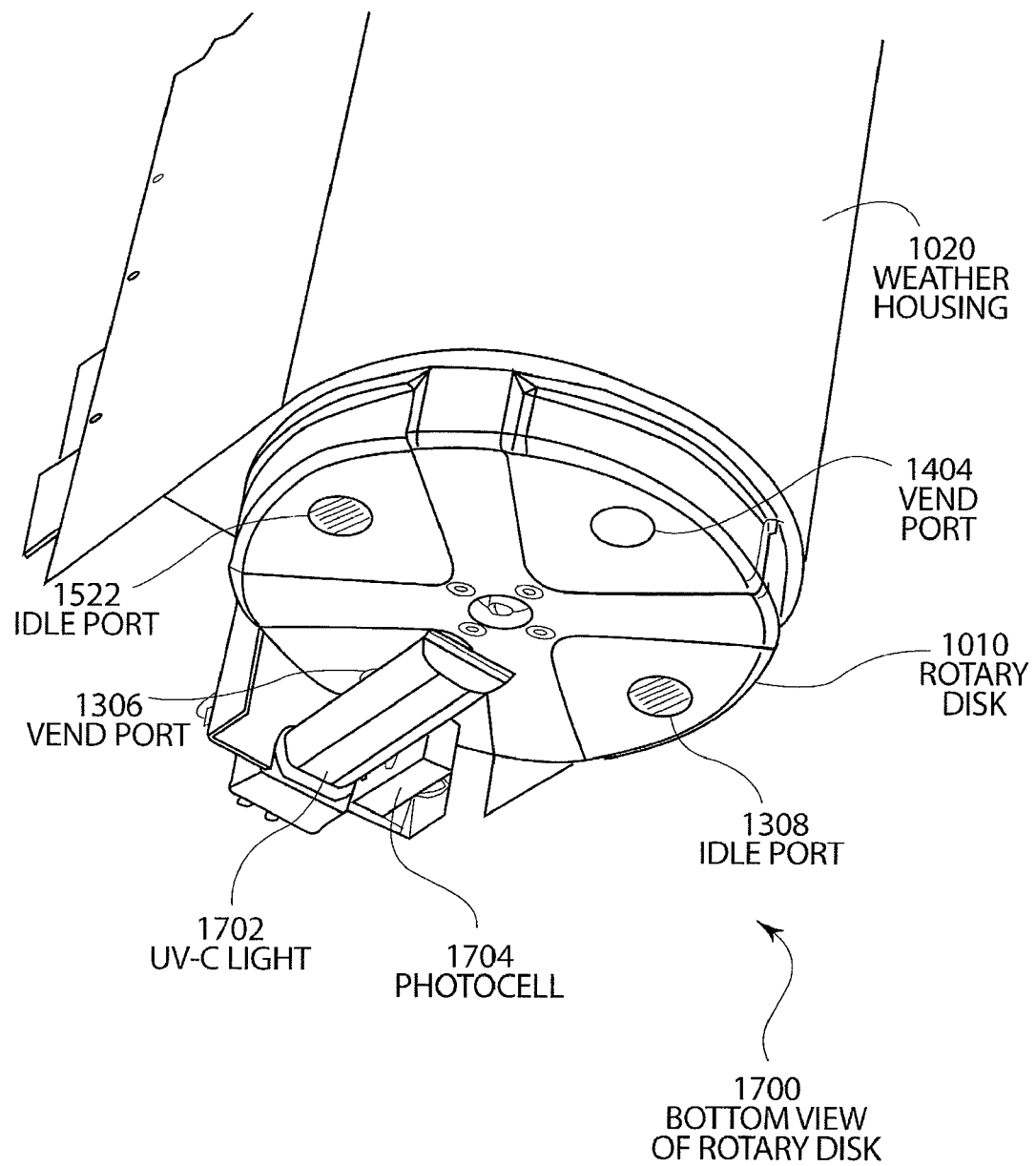
FIG. 17 is an isometric diagram of a bottom view of an embodiment of the rotary disc.

FIG. 17 is a schematic bottom view 1700 of an embodiment of rotary disk 1010. As shown in FIG. 17, the rotary disk is located below the weather housing 1020 and provides a physical barrier for accessing the interior of the weather housing 1020. UV-C light 1702 is located below the rotary disk 1010 and is aligned with the vend port 1306. UV-C light 1702 includes a UV-C bulb 1518 (FIG. 15) that irradiates the vend port 1306 from the bottom of the rotary disk 1010 and disinfects the surfaces surrounding the vend port 1306. UV-C light 1702 irradiates only one quadrant of the rotary disk 1010 at a time. As also shown in FIG. 17, vend port 1404 is located opposite to the vend port 1306 at 180° around the surface of the rotary disk 1010. Located at 90° in each direction around the surface of the rotary disk 1010, are idle port 1522 and idle port 1308. Photocell 1704 detects whether the UV-C light 1702 is operating and generates an error message if no light signal is detected during the time that the UV-C light 1702 is turned on. The error message is then sent to the central office via the communication link, such as the Internet.

Figure 18:
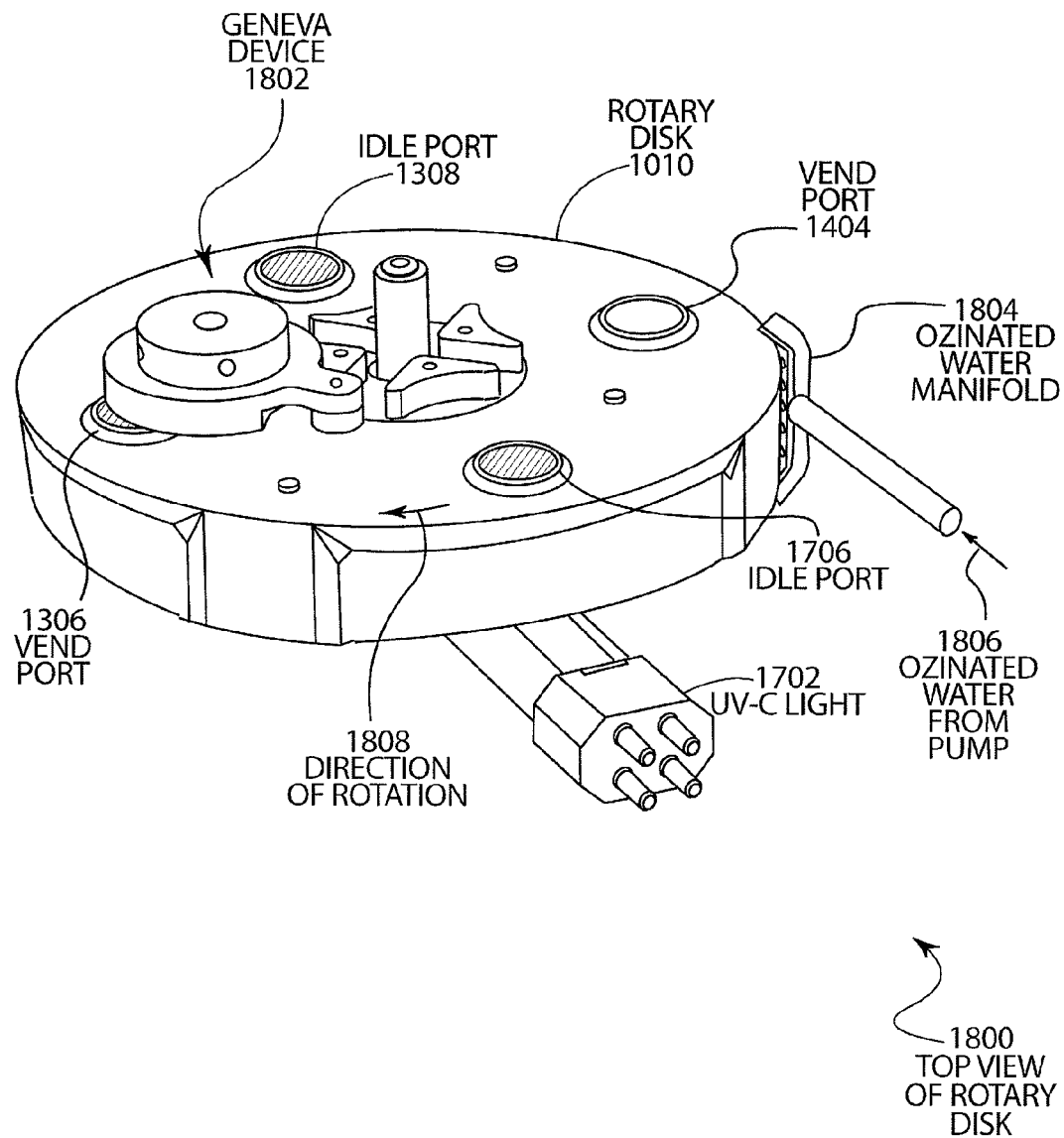
FIG. 18 is an isometric diagram of an embodiment of a rotary disc, as viewed from the top of the rotary disc.

FIG. 18 is a top view 1800 of the rotary disk 1010 illustrating another embodiment for sanitizing the rotary disk 1010. As shown in FIG. 18, an ozinated water manifold 1804 is disposed on a lateral portion of the rotary disk 1010. Ozinated water manifold 1804 supplies a high pressure spray of ozinated water 1806 from a pump (not shown). The ozinated water from the ozinated water manifold 1804 rinses the side, top and bottom surfaces of the rotary disk 1010 as the rotary disk rotates during each vend cycle. The ozinated water from the ozinated water manifold 1804 flows over the top and bottom surfaces of the rotary disk 1010 including the surfaces of the idle ports 1308, 1706 and the inside surfaces of the vend ports 1306, 1404. The direction of rotation shown by arrow 1808 causes the rotary disk 1010 to be cleaned and disinfected immediately after the completion of the vend cycle. The consumer and the rest of the components of the dispenser 1008 are isolated from the ozinated water spray by partitions (not shown) that prevent the spray from extending to other portions of the dispenser 1008. The residual action of the ozone in the water solution is effective as a disinfectant. The mechanical stripping action of the high pressure spray together with the disinfectant action of the ozone results in the rotary disk 1010 being thoroughly cleaned and decontaminated. A diverter valve can be used in the drain port to route the ozinated rinse water to a collection system where the fluid can be filtered and recycled for later use. A drain flow switch 2904 (FIG. 29) can be used in the drain line to monitor and confirm that the ozone fluid rinse station is operating properly. A UV-C light 1702 can also be used in conjunction with the ozinated water manifold 1804 to provide further disinfection. FIG. 18 also illustrates the geneva drive 1802 that is described in more detail below.

Figure 19:
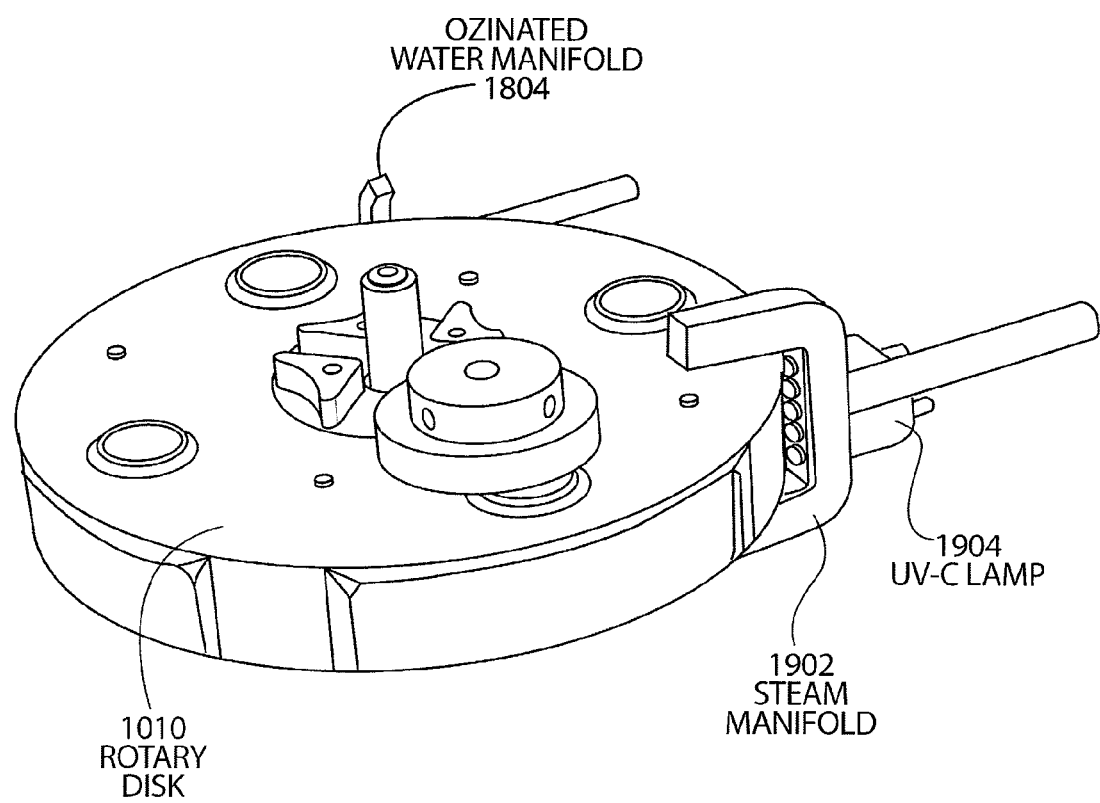
FIG. 19 is another isometric diagram of an embodiment of a rotary disc, as viewed from the top.

FIG. 19 illustrates another embodiment in which a steam manifold 1902 is used to further strip and disinfect the rotary disk 1010. As shown in FIG. 19, three different types of cleaning and disinfecting methods can be used, including the ozinated water manifold 1804, the UV-C lamp 1904 and the steam manifold 1902. The steam generated by the steam manifold 1902 has both a stripping action and a disinfecting action as a result of the high temperature steam that is applied to the surface of the rotary disk 1010. The steam manifold may have arms that extend sufficiently inwardly along the surface of the rotary disk 1010 on both the top and the bottom to ensure that the vend ports are adequately disinfected. The steam from the steam manifold 1902 also has a beneficial effect of heating the rotary disk 1010 to accelerate drying of the surface. Steam manifold 1902 is partitioned from the outside of the dispenser 1008 so that there is no human contact and can be partitioned to ensure that the steam does not reach other portion of the dispenser 1008.

Figure 20:
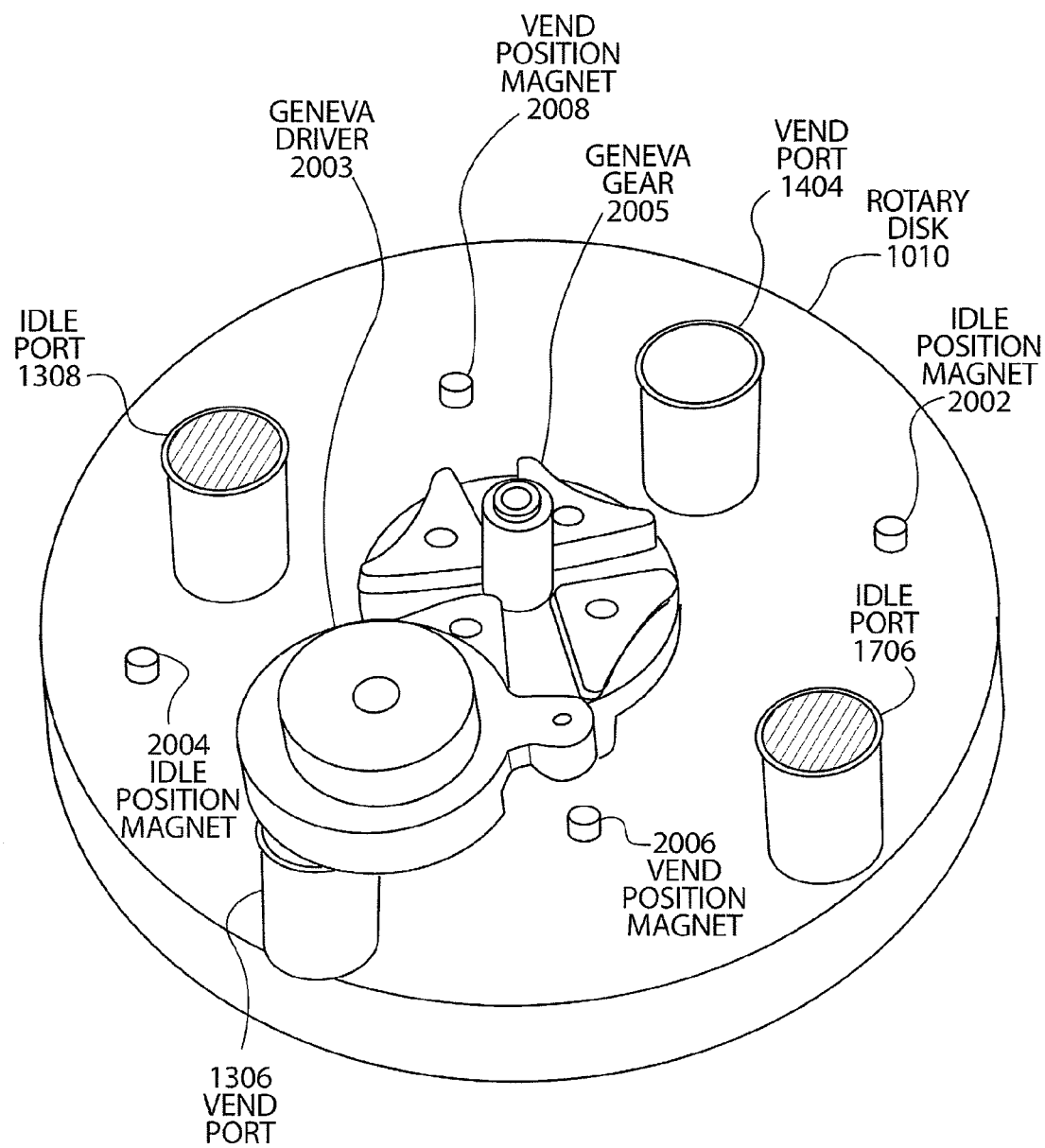
FIG. 20 is another isometric diagram of a rotary disc.

FIG. 20 is a schematic diagram illustrating the geneva device and position magnets that assist in controlling the operation of the rotary disk 1010. As shown in FIG. 20, vend ports 1306 and 1404 are located in opposite quadrants of the rotary disk 1010. Similarly, idle ports 1308, 1706 are located in opposite quadrants and are disposed between the vend ports 1306, 1404 on the rotary disk 1010. Idle position magnet 2002 and idle position magnet 2004 are disposed between vend port 1404 and idle port 1706 and idle port 1308 and vend port 1306, respectively, in opposing locations in opposite quadrants on the rotary disk 1010. Vend position magnet 2006 and vend position magnet 2008 are located in opposite quadrants that are interdisposed between the quadrants of the idle position magnets 2002, 2004. As can be seen from FIG. 20, the vend position magnets 2006, 2008 are disposed in equal pre-selected distance from the center of the rotary disk 1010. Idle position magnets 2002, 2004 are also disposed a pre-selected distance from the center of the rotary disk 1010, which is greater than the pre-selected distance of the vend position magnets 2006, 2008 from the center of the rotary disk 1010. In this manner, the idle position magnets 2002, 2004 can be detected separately from the vend position magnets 2006, 2008 during rotation of the rotary disk 1010 by placing detectors at a farther distance from the center of the rotary disk 1010. The geneva device illustrated in FIG. 20 includes a geneva driver 2003 and a geneva gear 2005. The operation of the geneva device is explained in more detail below.

Figure 21:
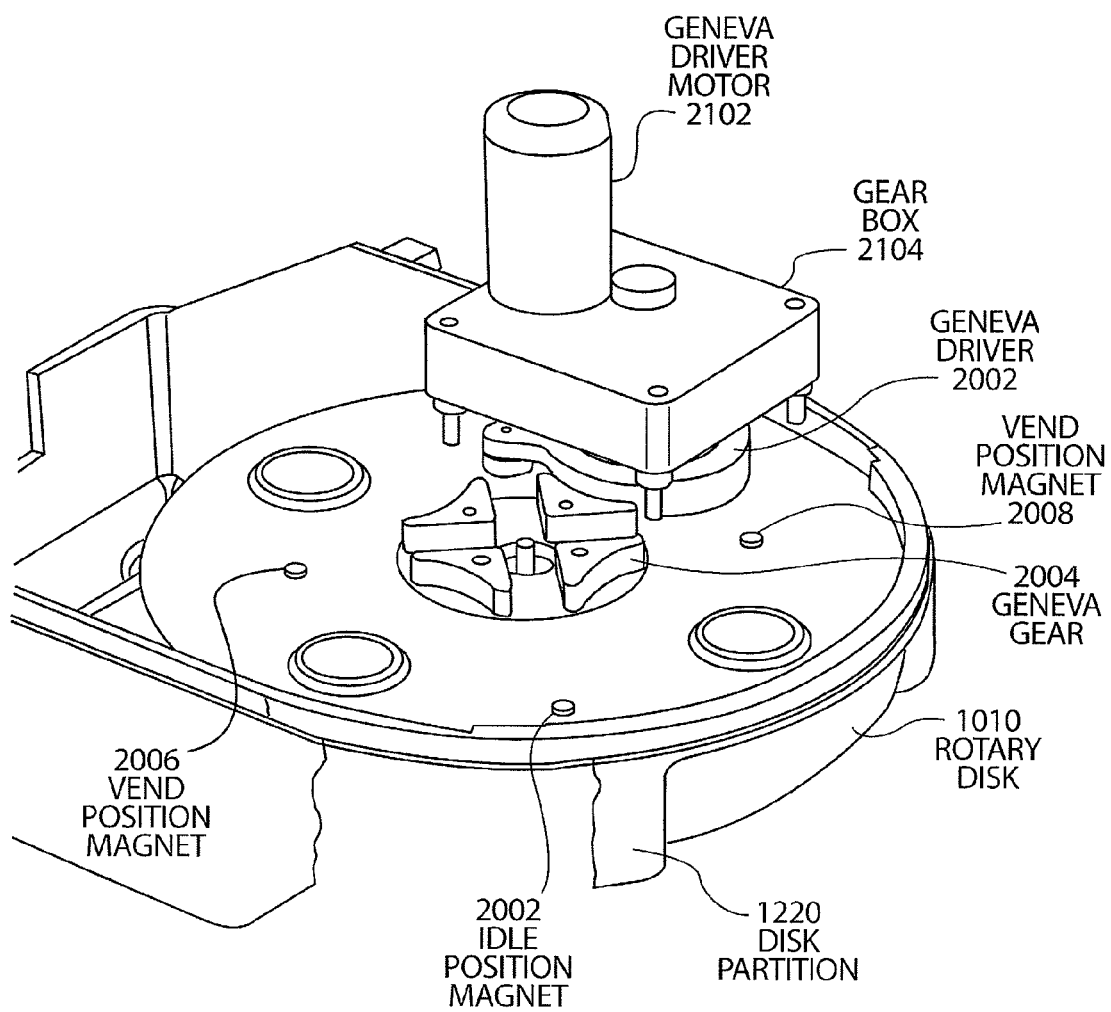
FIG. 21 is another view of the embodiment of the rotary disk and geneva unit.

FIG. 21 further illustrates the geneva mechanism and position magnets. As shown in FIG. 21, the geneva mechanism includes a geneva driver motor 2102 that drives a gear box 2104. A gear box 2104 is connected to the geneva driver motor 2002 that interacts with the geneva gear 2004. FIG. 21 also illustrates the vend position magnets 2006, 2008, the idle position magnet 2002, the rotary disk 1010 and the disk partition 1220. The geneva driver motor 2102 is driven by signals from the control unit 3202 that controls the operation of the dispenser 1008. The Genera driver motor 2102 operates in response to a variable pulse-width power supply. The control system 3200 (FIG. 32) changes the speed and torque of the rotation of the geneva drive motor 2102 by alternating the duty cycle of the power signal as a result of the process of changing the pulse-width. The geneva driver motor 2102 is normally powered with minimum torque as a safety precaution to ensure that fingers are not injured during rotation of the rotary disk 1010 if they are inserted in a vend port. In the event that a problem is detected in the rotation of the rotary disk 1010, the torque of the geneva driver motor 2102 can be increased or the direction of the geneva driver motor 2102 can be reversed to clear any mechanical jams. If the rotation of the rotary disk 1010 fails after a predetermined number of retries, a malfunction is reported, and the unit can be placed in an extended error recovery state.

Figure 22:
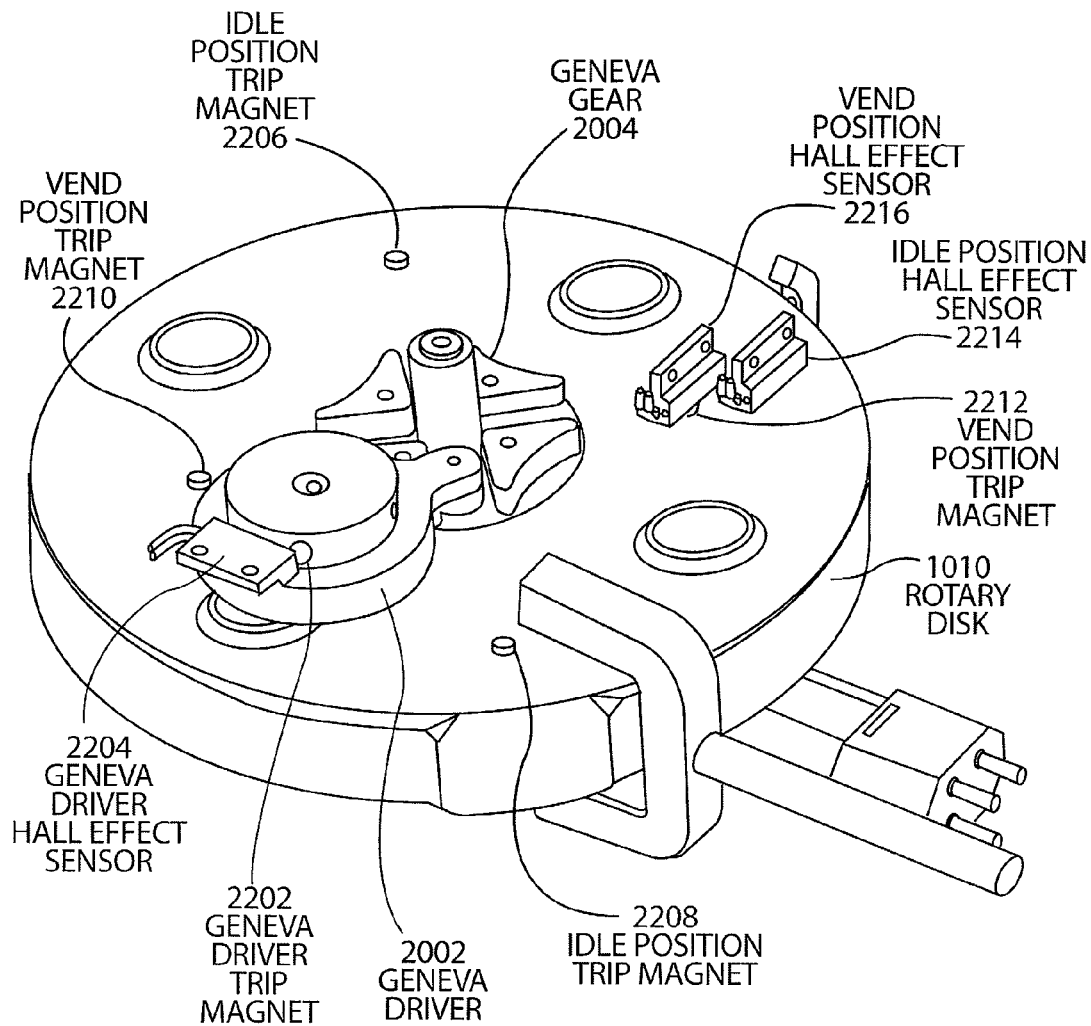
FIG. 22 is another isometric view of an embodiment of the rotary disk and geneva unit.

FIG. 22 illustrates the manner in which the rotation of the rotary disk 1010 may be detected in accordance with one embodiment. As shown in FIG. 22, the geneva driver 2002 includes a geneva driver trip magnet 2202 located on a raised disk portion of the geneva driver 2002. A geneva driver hall effect sensor 2204 is located adjacent the raised disk section and detects the presence of the geneva driver trip magnet 2202 during each full rotation of the geneva driver 2003. The geneva driver hall effect sensor 2204 generates an electrical signal that is used by the control system to activate and deactivate the geneva driver motor 2102 (FIG. 21) for each full 360 degree rotation of the geneva driver 2003. The geneva gear 2005 is connected to the rotary disk 1010 and turns a full 90 degrees for each 360 degree rotation of the geneva driver 2003, as explained in more detail below.

As also shown in FIG. 22, vend position trip magnets 2210, 2212 are spaced a predetermined distance from the center of the rotary disk 1010 to be detected by vend position hall effect sensor 2216. Each time one of the vend position trip magnets 2210, 2212 passes below the vend position hall effect sensor 2216, the vend position hall effect sensor 2216 generates a signal indicating that the rotary disk 1010 is in the vend position. Similarly, idle position magnets 2206, 2208 are detected by the idle position hall effect sensor 2214 which is spaced the same distance from the center of the rotary disk 1010 as the idle position trip magnets 2206, 2208. By using different spacings of the vend trip magnets 2210, 2212 and the idle position trip magnets 2206, 2208 from the center of the rotary disk 1010, the vend position hall effect sensor 2216 and the idle position hall effect sensor 2214 are able to separately detect when the rotary disk 1010 is in the vend position or idle position, respectively.

Figure 23:
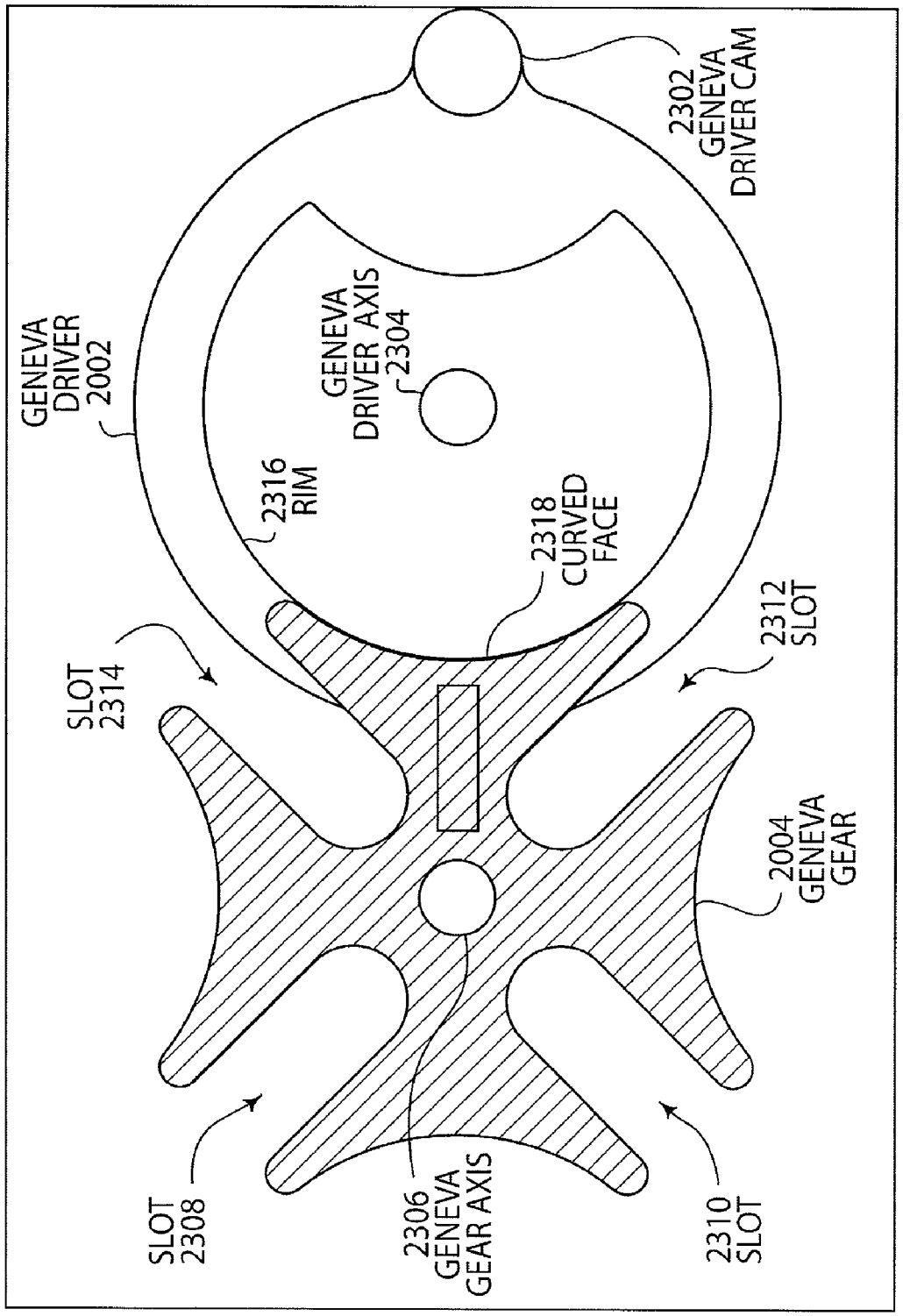
FIGS. 23-27 are a top view of the geneva driver and geneva gear illustrating the manner in which the geneva unit operates.

FIG. 23 is a schematic illustration of the geneva driver 2002 and the geneva gear 2004. As shown in FIG. 23, the geneva gear 2004 has a curved face 2318 that intersects and is held by the rim 2316 of the geneva driver 2002 to prevent rotation of the geneva gear 2004. As the geneva driver 2002 rotates around the geneva driver axis 2304, the geneva gear 2004 is held in place and cannot rotate around the geneva gear axis 2306. The geneva gear 2004 has slots 2308, 2310, 2312 and 2314 that are spaced between the curved face surfaces of the geneva gear 2004. geneva driver 2002 includes a geneva driver cam 2302 that interfaces with the slots 2308, 2310, 2312 and 2314, as disclosed below.

Figure 24:
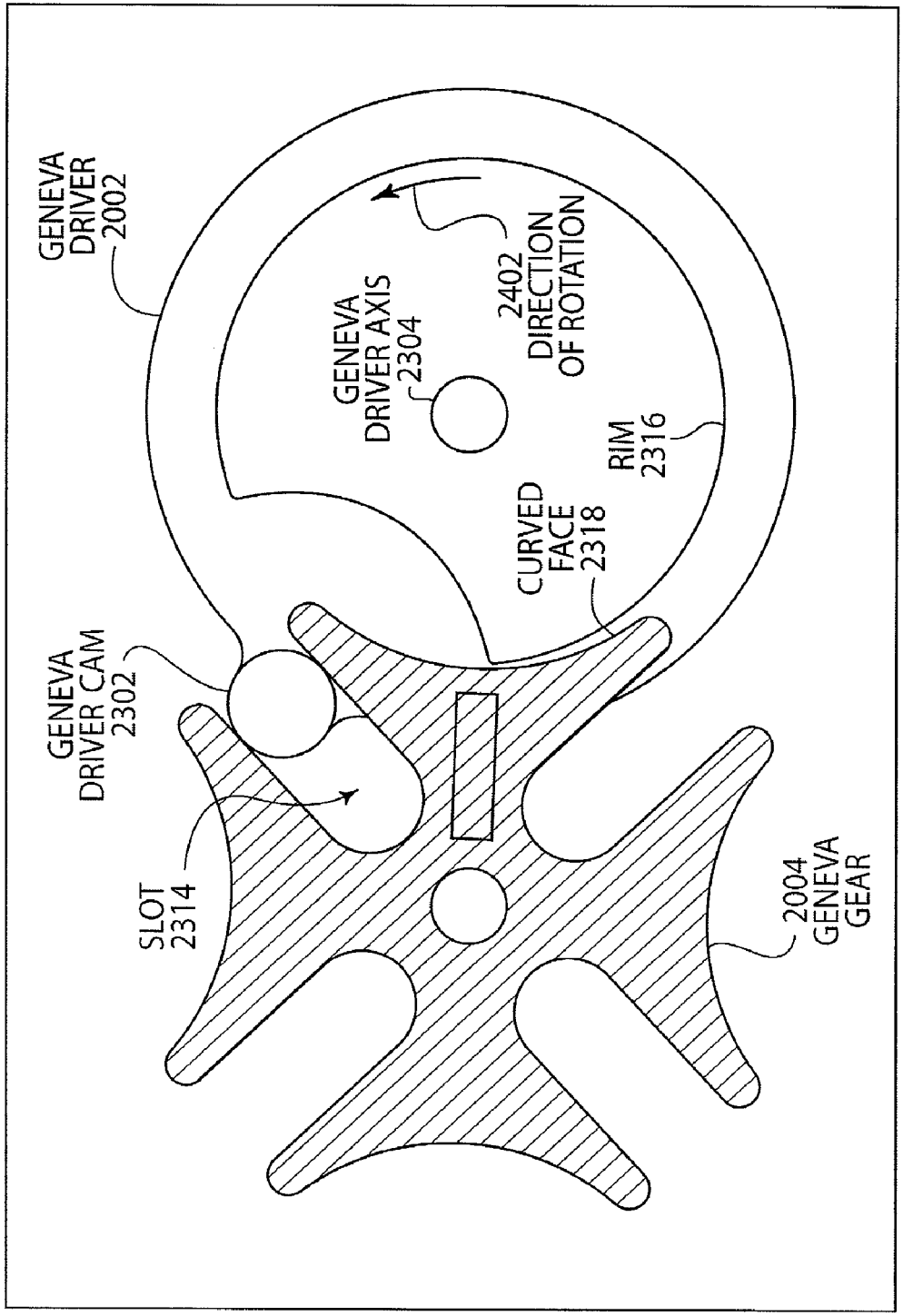

FIG. 24 illustrates the manner in which the geneva driver cam 2302 intersects the slot 2314 of the geneva gear 2004 as the geneva driver 2002 rotates in the direction of rotation 2402. As shown in FIG. 24, the rim 2316 engages the curved face 2318 of the geneva driver 2002 until the geneva driver cam 2302 engages the slot 2314.

Figure 25:
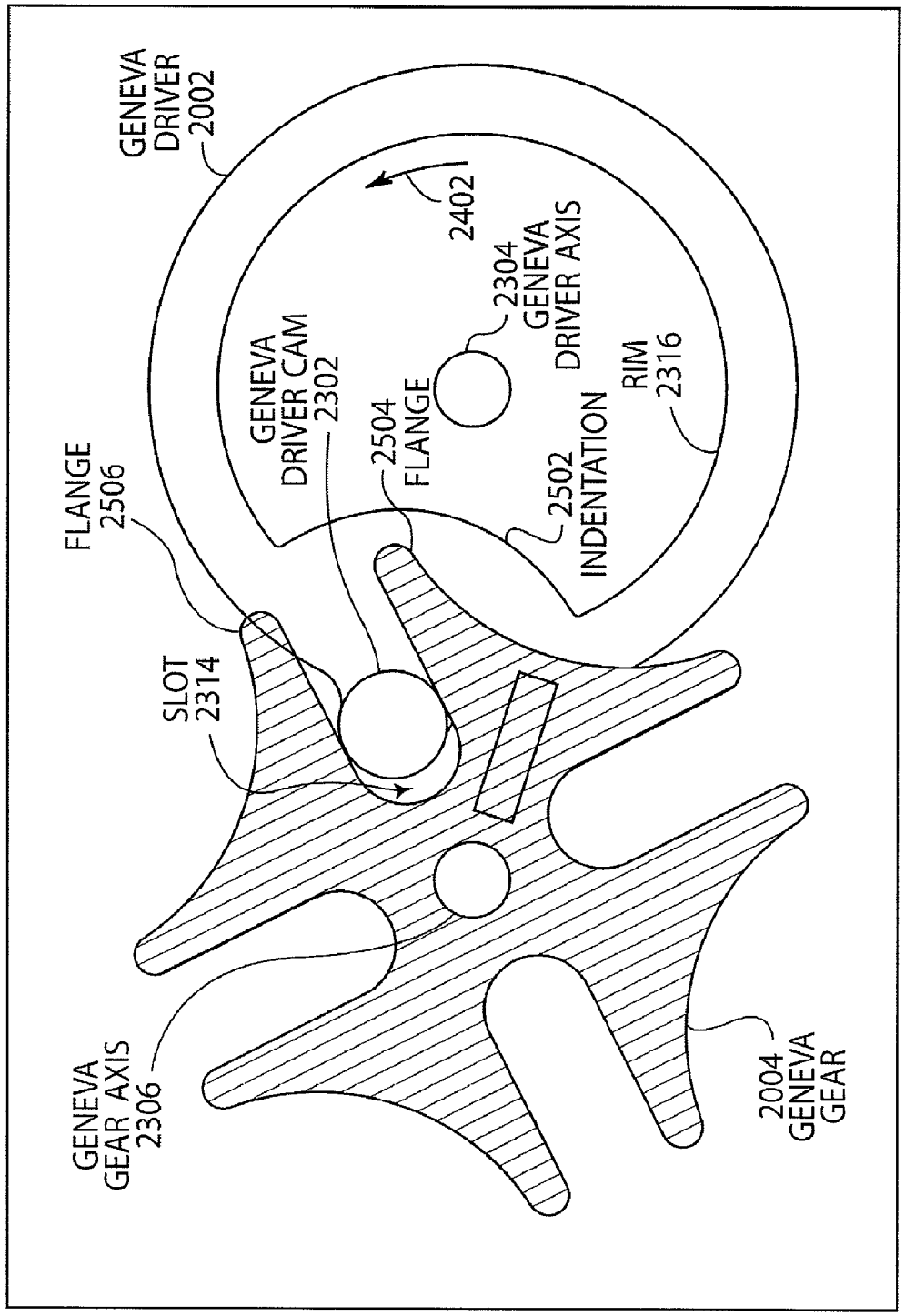

As shown in FIG. 25, the geneva driver 2002 is rotated further in the direction of rotation 2402 around the geneva driver axis 2304. The geneva driver cam 2302 further engages the slot 2314 and causes the geneva gear 2004 to further rotate around the geneva gear axis 2306. As also shown in FIG. 25, the rim 2316 includes an indentation 2502 that allows flange 2504 and flange 2506 to clear (not intersect) the rim 2316 as the geneva gear 2004 rotates around the geneva gear axis 2306.

Figure 26:
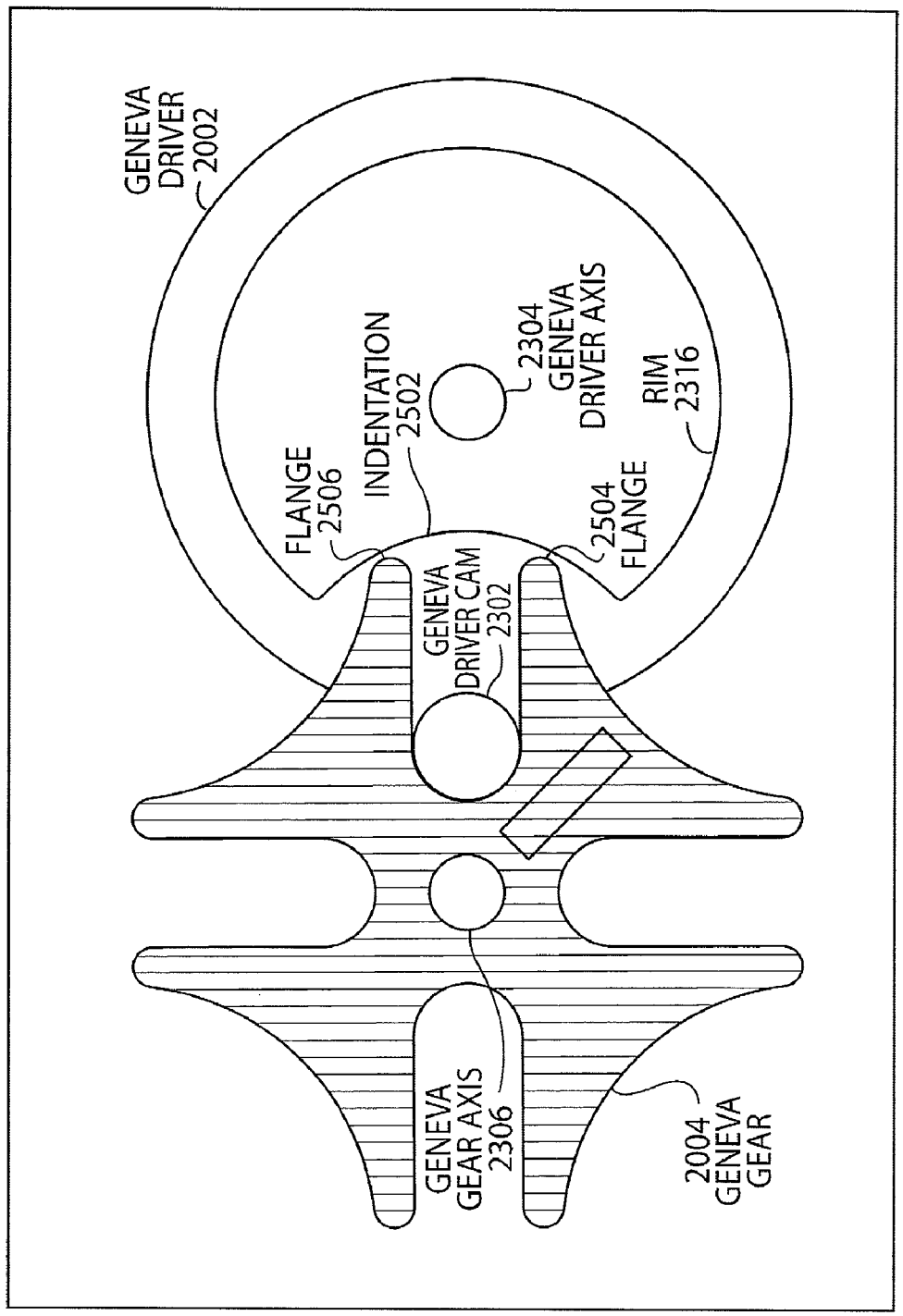

FIG. 26 illustrates the geneva driver 2002 in a further rotated position. As shown in FIG. 26, the geneva driver cam 2302 is fully engaged in the slot 2314 and the geneva gear 2004 is rotated by 45 degrees on the geneva gear axis 2306. The geneva driver 2002 is rotated a full 180 degrees. Flanges 2504, 2506 do not interfere with the rim 2316 because of the indentation 2502.

Figure 27:
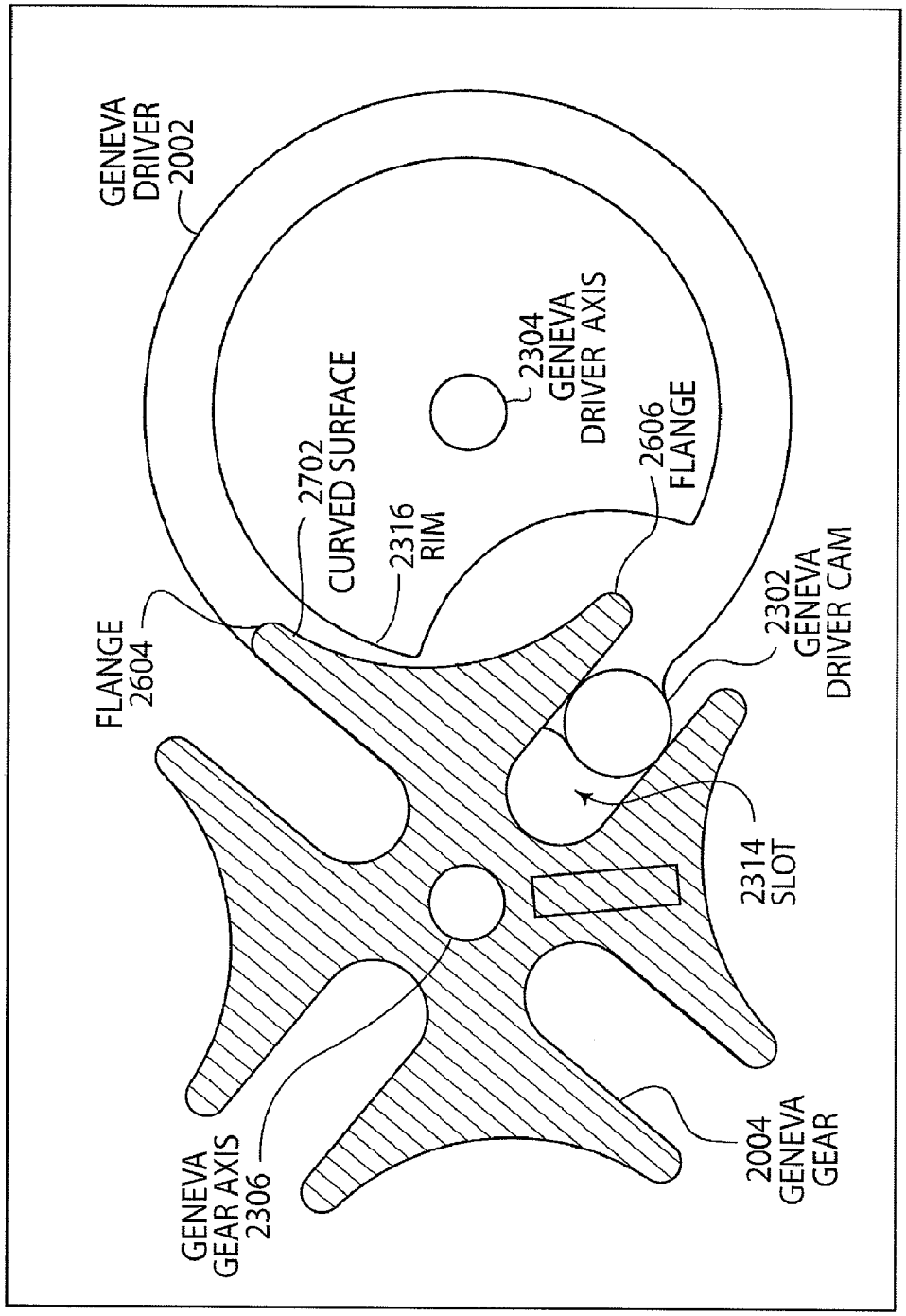

FIG. 27 illustrates the geneva driver 2002 in a further rotated position. As shown in FIG. 27, the geneva driver cam 2302 has further rotated the geneva gear 2004 around the geneva gear axis 2306. Rim 2316 is shown just prior to engagement of curved surface 2702. As the geneva driver cam 2302 rotates out of the slot 2314, rim 2316 fully engages the curved surface 2702 so that the geneva gear 2004 is fully rotated by 90 degrees.

Figure 28:
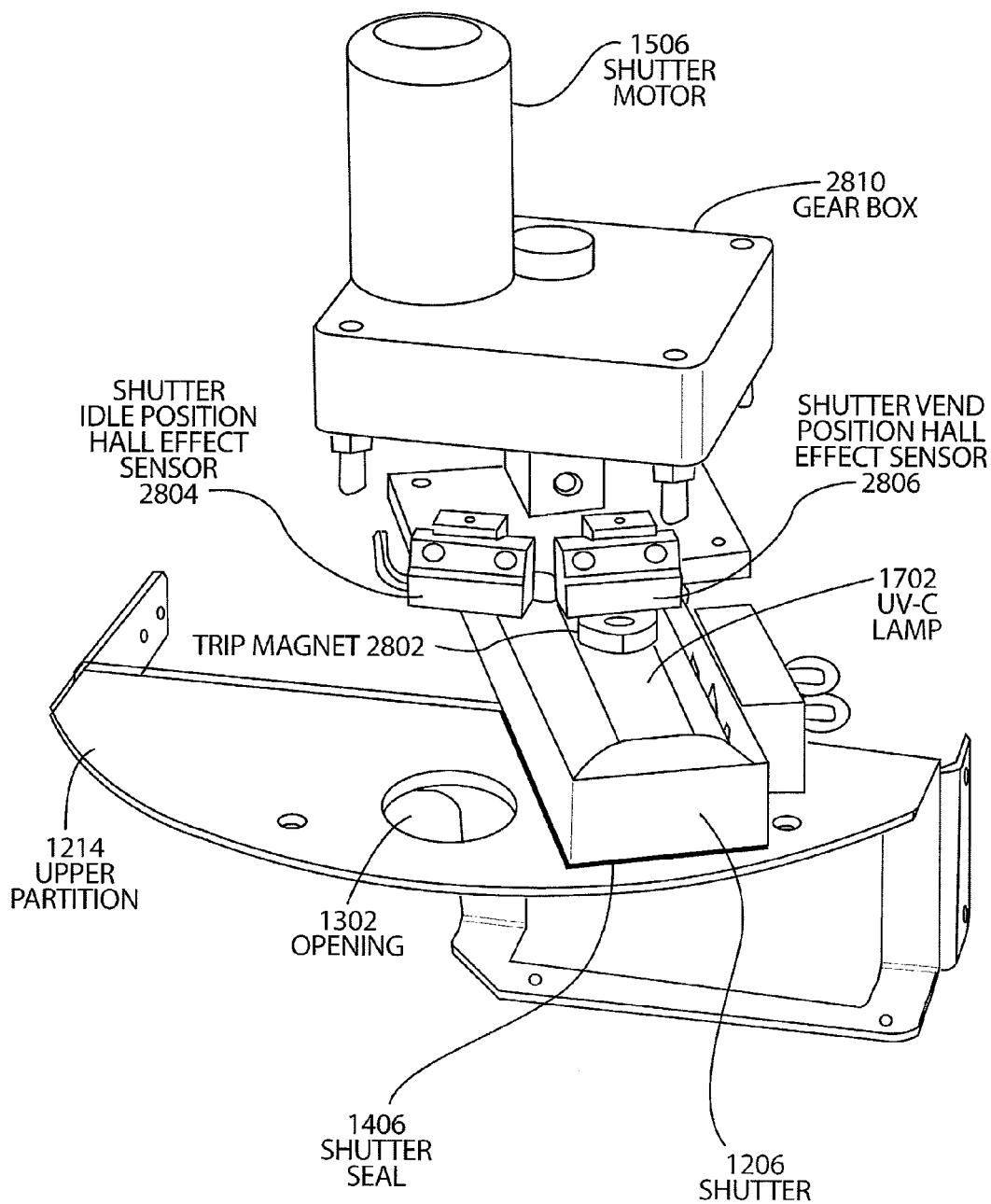
FIG. 28 is an isometric view of an embodiment of the shutter assembly.

FIG. 28 is a schematic illustration of one embodiment of a shutter mechanism. As shown in FIG. 28, the shutter 1206 is in the vend position, such that the opening 1302 is not covered by the shutter 1206. Shutter 1206 has a shutter seal 1406 that seals the shutter 1206 to the upper partition 1214 and covers the opening 1302 when the shutter 1206 is in the idle position. Shutter 1206 has a UV-C lamp 1702 that shines upwardly and disinfects the point of vend 1202 (FIG. 12). The shutter 1206 is operated by the shutter motor 1506, which is connected to gear box 2810. Gear box 2810 moves the shutter 1206 between the vend position illustrated in FIG. 28 and the idle position. Trip magnet 2802 is detected by the shutter vend position hall effect sensor 2806 when the shutter 1206 is in the vend position, as illustrated in FIG. 28. A signal is generated by the shutter vend position hall effect sensor 2806 and is sent to the control unit 3202 (FIG. 32) to indicate that the shutter 1206 is in the vend position. Similarly, shuttle idle position hall effect sensor 2804 detects the trip magnet 2802 when the shutter 1206 is in the idle position and the trip magnet 2802 is proximate to the shutter idle position hall effect sensor 2804. Shutter idle position hall effect sensor 2804 generates an electrical signal upon detection of the trip magnet 2802, which is received by the control unit 3202 (FIG. 32) that identifies the shutter 1206 as being in the idle position. When the shutter 1206 is in the idle position, the shutter and the shutter seal 1406 provide a physical barrier, which is a deterrent to tampering. If the shutter sensors 2804, 2806 change without a command from the control unit 3202 (FIG. 32), a malfunction is reported. This may occur when there is evidence of mechanical tampering or a system error. When the control unit 3202 (FIG. 32) generates a command to move the shutter, the control unit 3202 (FIG. 32) sets a timer in anticipation of the arrival of the shutter in its new position. If the shutter sensors 2804, 2806 fail to respond and generate a signal within the expected time interval, a malfunction is reported. At that point, the control unit 3202 (FIG. 32) may cycle the dispenser for error recovery.

Figure 29:
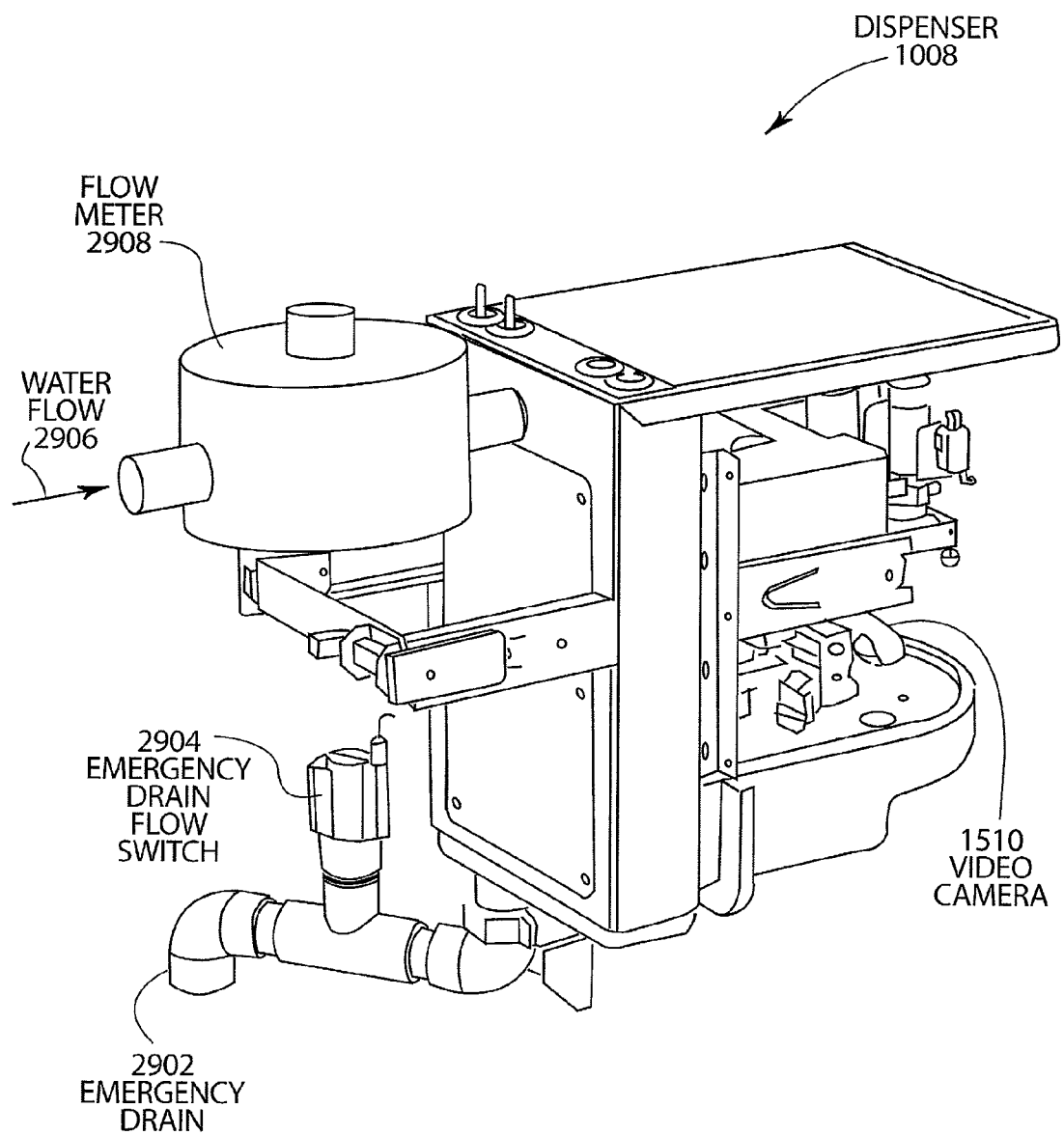
FIG. 29 is an isometric view of an embodiment of various water flow devices that are used with the dispenser.

FIG. 29 illustrates an embodiment disclosing several of the water flow mechanisms. As shown in FIG. 29, there is a supply of water 2906 that flows into a flow meter 2908 that measures and supplies the water to the dispenser 1008. Upon initiation of the vend cycle, the shutter 1206 (FIG. 28) is moved from the idle position, over opening 1302 (FIG. 28), to the vend position that is illustrated in FIG. 28. At approximately the same time, the rotary disk 1010 is rotated so that a vend port, such as vend port 1306 (FIG. 13), is aligned with opening 1304, opening 1302, and point of vend 1202, as illustrated in FIG. 13. The vend position hall effect sensor 2216 then confirms that the rotary disk 1010 is in the vend position and the geneva driver hall effect sensor 2204 indicates that the geneva driver is in the proper position, as shown in FIG. 22. A control signal is then sent to a water pump that pressurizes the water path. Subsequently, a signal is sent to the vend valve solenoid 1210 to open the vend valve 1208 to cause the pressurized water to flow to the check valve 1602 (FIG. 16). When the water reaches a certain pressure on check valve 1602, the check valve 1602 opens and water flows through the laminar flow insert 1604 through the point of vend 1202, as illustrated in FIG. 16. A solid and smooth column of water in a defined stream 1204 is then emitted from the point of vend 1202. The control system monitors the water flow from signals generated by flow meter 2908, as shown in FIG. 29. Once the desired quantity of water has been dispensed, a control signal is sent to the water pump to shut off the water pump. Shortly thereafter, a signal is sent to the vend valve solenoid 1210 to close the vend valve 1208. Once the water pressure falls below a predetermined value, the check valve 1602 (FIG. 16) closes and the flow of water stops from the point of vend 1202. Since the check valve 1602 is located close to the point of vend 1202, additional water does not flow from the point of vend 1202 and is promptly shut off, so that there is no dribbling of water. The rotary disk 1010 is then rotated to the idle position and the shutter 1206 (FIG. 28) is moved to the idle position over the opening 1302 (FIG. 28). A timer is then set and the control system waits for a signal from the idle position hall effect sensor 2214 indicating that either the idle position trip magnet 2208, or the idle position trip magnet 2206, is proximate to the idle position hall effect sensor 2214, and the rotary disk 1010 is in the idle position. If this does not occur within a certain time period, an error condition is reported.

FIG. 29 also discloses an emergency drain 2902 and an emergency drain flow switch 2904. Any spills that occur are routed to the emergency drain 2902. If an unexpected water flow is detected by the emergency drain flow switch 2904, such as when the flow of water is impeded through one of the vend ports 1306, 1404, as a result of an obstruction, emergency drain flow switch 2904 generates a signal that is reported as a malfunction by the control unit 3202 (FIG. 32). When the water pump, that pumps the water through the system, and the vend valve solenoid 1210 (FIG. 16) receive a command to open, a timer is set by the control unit 3202 (FIG. 32) in anticipation of water flow being reported by the flow meter 2908. If the expected water flow does not occur, a malfunction is reported. Further, if the rate of flow through the flow meter 2908 is above or below an expected range, a malfunction is reported. At the end of each vend cycle, video camera 1510 inspects the vend port, after the rotary disk 1010 is locked into the idle position. If an obstruction or physical contaminant is observed in one of the vend ports, a malfunction is reported.

Figure 30:
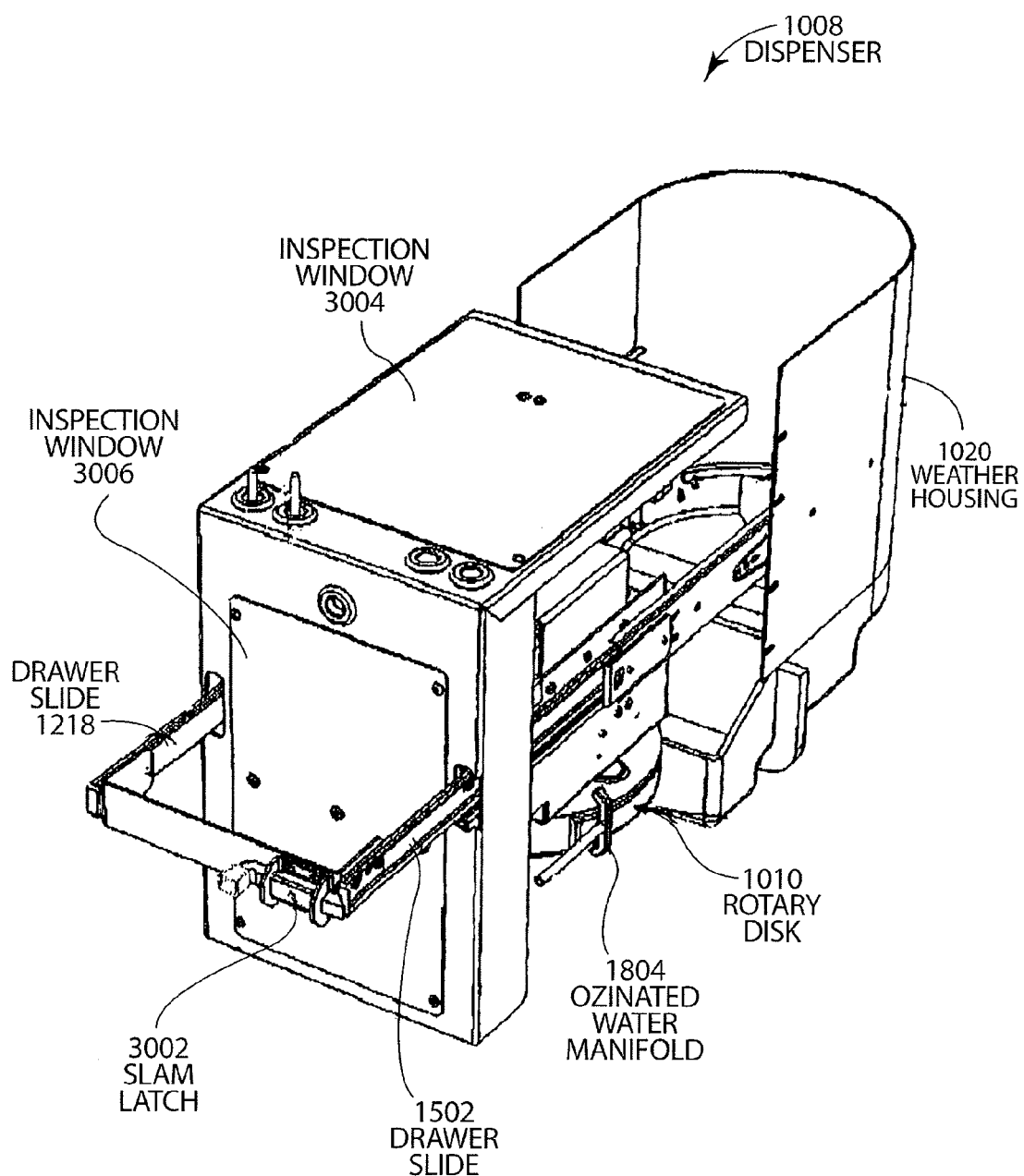
FIG. 30 is an isometric view of an embodiment of the dispenser in the open or service position.

FIG. 30 is a schematic illustration of the dispenser 1008 in an open position for inspection and service. Inspection windows 3004 and 3006 allow visible observation of the interior of the dispenser 1008. Slam latch 3002 normally holds the dispenser 1008 in a closed (operating) position. Once the slam latch 3002 is released, the mechanism can be opened using drawer slides 3008, 3010. Drawer slides 1218, 1502 allow the dispenser mechanism to be separated from the weather housing 1020 to allow easy service and inspection. In the open or service position illustrated in FIG. 30, safety interlock switches disable power to the automatic disinfection systems, such as the ozinated water manifold 1804 (FIG. 18), the UV-C light 1702 (FIG. 17) and the steam manifold 1902 (FIG. 19). In the service position illustrated in FIG. 30, there is a direct line of sight to all of the surfaces of the rotary disk 1010 that are normally exposed to the outside environment.

Figure 31:
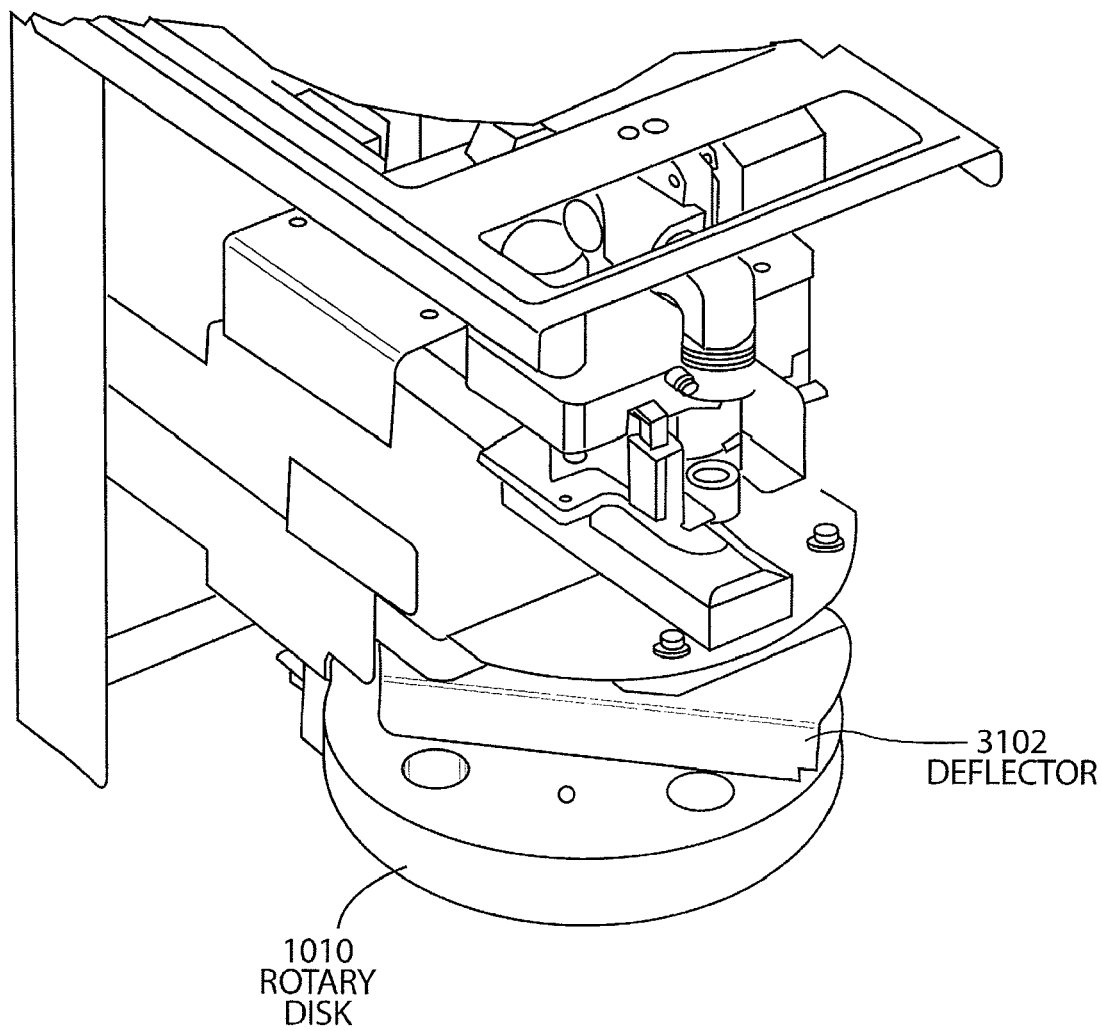
FIG. 31 is an isometric view of the dispenser unit illustrating the deflector.

FIG. 31 illustrates the deflector 3102 that is adjacent the rotary disk 1010. Deflector 3102 deflects any objects that may have been lodged or fallen onto the top of the rotary disk 1010. These objects are deflected into a receptacle area, so that they do not cause an obstruction. Deflector 3102 is raised slightly off of the surface of the rotary disk 1010, so that virtually all objects are deflected from the surface of the rotary disk 1010.

FIG. 32 is a schematic block diagram of the control system of the embodiment illustrated in FIG. 10. As shown in FIG. 32, a control system 3202 may comprise a standard computer control system. It has communication ports 3218, 3220 for communicating command and control signals and information to and from dispenser 3204 and sending and receiving information over the Internet 3206, respectively. A local keyboard 3208 is provided with the control system for manual entry of data by service personnel or other individuals. Information from the coin mechanism 3212, the bill accepter 3214 and card reader 3216 is received by the control system 3202. The water tank 3210 is connected to the dispenser 3204 and dispenses water as a result of commands received over communication path 3218.

The embodiment disclosed herein therefore provides a system for dispensing water or any type of desired fluid or other materials in a manner that sanitizes the valve ports and valve port openings to prevent the spread of contamination. In addition, the feedback and communication systems such as the use of a camera, hall effect sensors and a backflow detector provide information to determine if the rotary valve disk 136 is operating properly, if any tampering has occurred, or if there is any blockage of the valve ports 140, 142. These feedback devices also allow for detection of proper orientation of the rotary valve disk 136 so that a service technician can also be called when the system is not operating properly.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A dispenser for dispensing a fluid to a user into a container at a user access point in a fluid dispensing stream comprising: a point of vend port that dispenses said fluid, said point of vend port disposed in a first isolation chamber; a second isolation chamber that provides spatial separation between said point of vend port and said user access point; a shutter that isolates said first isolation chamber from said second isolation chamber during an idle state; a UV lamp mounted on said shutter that irradiates and sanitizes said point of vend port during said idle state; a rotary disk having a vend port and an idle port, said vend port aligned with said point of vend port when said dispenser is in a vend state and said idle port aligned with said point of vend port when said dispenser is in an idle state, said rotary disk made of a clear plastic so that an alignment indicator is visible to said user during said idle state and during said vend state so that said user can align said container with said water dispensing stream during said idle state and said vend state, said rotary disk positioned adjacent to said second isolation chamber to provide a physical barrier between said user access point and said second isolation chamber; a driver that rotates said rotary disk between said idle state and said vend state.

2. The dispenser of claim 1 wherein said driver comprises a geneva driver coupled to a drive motor and a geneva gear coupled to said rotary disk.

3. The dispenser of claim 2 further comprising:
   a light that illuminates said clear portion of said rotary disk so that said idle port and said vend port are illuminated and visible to said user during said idle state and said vend state.

4. The dispenser of claim 3 further comprising:
   a first disk UV lamp disposed adjacent to a first side of said rotary disk that irradiates and sanitizes said first side of said rotary disk;
   a second disk UV lamp disposed adjacent to a second side of said rotary disk that irradiates and sanitizes said second side of said rotary disk.

5. The dispenser of claim 4 further comprising:
   an ozinated water manifold disposed adjacent to said rotary disk that sprays said rotary disk with an ozinated water spray that strips and sanitizes said rotary disk.

6. The dispenser of claim 5 further comprising:
a steam manifold disposed adjacent to said rotary disk that emits steam that strips and sanitizes said rotary disk.

7. A method of dispensing fluid from a dispenser to a user into a container at a user access point in a fluid stream comprising: isolating a point of vend port that dispenses said fluid from said user access point with a rotary disk that forms a physical barrier between said point of vend port and said user access point; isolating said point of vend port from said rotary disk with a shutter that forms a physical barrier between said point of vend port and said user access point during an idle state of said dispenser; irradiating said point of vend port during said idle state with a UV lamp mounted on said shutter; aligning an idle port in said rotary disk with said point of vend port during an idle state so that said container can be aligned by a user with said fluid stream during said dispensing of said fluid; aligning a vend port in said rotary disk with said point of vend port during a vend state so that said fluid stream passes from said point of vend port through said vend port during said vend state; providing said rotary disk as a clear plastic so that an indicator is visible to said user during said vend state and said idle state so that said user can align said container with said fluid stream during said idle state; rotating said rotary disk so that said vend port is aligned with said point of vend port during said vend state and said idle port is aligned with said point of vend port during said idle state.

8. The method of claim 7 wherein said process of rotating said rotary disk is performed by a geneva driver coupled to a drive motor and a geneva gear coupled to said rotary disk.

9. The method of claim 8 further comprising:
illuminating said clear portion of said rotary disk so that said vend port and said idle port are visible to said user.

10. The method of claim 9 further comprising:
illuminating a lower portion of said rotary disk with a UV light to sterilize said lower portion of said rotary disk;
illuminating an upper portion of said rotary disk with a UV light to sterilize said upper portion of said rotary disk.

11. The method of claim 9 further comprising:
sterilizing said rotary disk with an ozinated water spray.

12. The method of claim 10 further comprising:
sterilizing said rotary disk with steam.

* * * * *